US011890380B1

(12) United States Patent
Al-hejaili et al.

(10) Patent No.: US 11,890,380 B1
(45) **Date of Patent: *Feb. 6, 2024**

(54) BUCCAL FORMULATION OF AVANAFIL WITH ENHANCED BIOAVAILABILITY AND PROLONGED DURATION

(71) Applicant: King Abdulaziz University, Jeddah (SA)

(72) Inventors: Omar D. Al-hejaili, Jeddah (SA); Khalid M. El-Say, Jeddah (SA); Tarek A. Ahmed, Jeddah (SA); Hossam S. El-Sawy, Jeddah (SA); Fathy I. Abd-Allah, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/191,259

(22) Filed: Mar. 28, 2023

Related U.S. Application Data

(62) Division of application No. 18/046,700, filed on Oct. 14, 2022, now Pat. No. 11,648,205.

(51) Int. Cl.

| | |
|---|---|
| ***A61K 9/20*** | (2006.01) |
| ***A61K 9/00*** | (2006.01) |
| ***A61K 31/506*** | (2006.01) |

(52) U.S. Cl.

CPC ............ *A61K 9/2027* (2013.01); *A61K 9/006* (2013.01); *A61K 9/2009* (2013.01); *A61K 9/2018* (2013.01); *A61K 9/2054* (2013.01); *A61K 9/2095* (2013.01); *A61K 31/506* (2013.01)

(58) Field of Classification Search

CPC .... A61K 9/2027; A61K 9/006; A61K 9/2009; A61K 9/2018; A61K 9/09; A61K 9/2054; A61K 9/2095; A61K 31/506

USPC ........................................................ 424/465

See application file for complete search history.

(56) References Cited

U.S. PATENT DOCUMENTS

| | | | | |
|---|---|---|---|---|
| 6,309,219 | B1 | 10/2001 | Robert | |
| 7,255,560 | B2 | 8/2007 | Bornstein | |
| 2006/0271077 | A1 | 11/2006 | Graser | |
| 2007/0265649 | A1 | 11/2007 | Perez | |
| 2009/0138027 | A1 | 5/2009 | Lucas et al. | |
| 2014/0074118 | A1 | 3/2014 | Esarey et al. | |
| 2018/0368870 | A1 | 12/2018 | Sanders | |
| 2020/0078307 | A1 | 3/2020 | Zhou et al. | |
| 2021/0315831 | A1* | 10/2021 | Martin | A61K 9/5146 |

FOREIGN PATENT DOCUMENTS

| | | | |
|---|---|---|---|
| JP | 2007-527275 | A | 9/2007 |
| KR | 2010-0061384 | A | 6/2010 |
| WO | 2020/171727 | A2 | 8/2020 |

* cited by examiner

*Primary Examiner* — Adam C Milligan

(74) *Attorney, Agent, or Firm* — WCF IP

(57) ABSTRACT

A buccal tablet formulation has a polyvinylpyrrolidone K-90 as a solid dispersion polymer, a hydroxypropyl methylcellulose as a mucoadhesive polymer, a sodium deoxycholate as mucopenetration enhancer, a porous silicon dioxide (e.g., FujiSil), mannitol, and avanafil. The ratio of PVP K-90 to AVA is approximately 2:1 (e.g., 2.3:1 to 1.7:1) in the tablet. Methods of making the buccal tablet with enhanced bioavailability and prolonged duration and methods of using the formulation for the treatment of erectile dysfunction are also provided.

2 Claims, 8 Drawing Sheets

BUCCAL FORMULATION OF AVANAFIL WITH ENHANCED BIOAVAILABILITY AND PROLONGED DURATION

FIELD OF INVENTION

The invention is generally related to the formulation of avanafil as a buccal tablet with enhanced bioavailability and a prolonged duration of action. Specifically, this formulation embodies a buccal route of administration to avoid hepatic first-pass metabolism and improve the drug bioavailability. This approach helps minimize the undesirable side effect in patients with erectile dysfunction.

BACKGROUND OF THE INVENTION

Impotence/erectile dysfunction (ED) is one of the most widely recognized diseases in male sexual dysfunction, with studies showing that ⅓ of American men over age 40 are affected with this disease (1,2). In Arab countries, recent studies showed that the prevalence of ED is more than 40% and is linked to various risk factors such as age, obesity, lack of activity, smoking, and diabetes mellitus complications (3,4). Locally in Jeddah, a cross-sectional, multi-clinical study showed that more than 70% of the participants in the study showed moderate to severe ED symptoms (5). It is not commonly seen as a life-threatening illness, but it is meticulously linked to several necessary physical conditions and can impact psychosocial well-being. Therefore, ED affects patients' quality of life (6). The main goals of ED management are to monitor and minimize risk factors associated with organic cardiovascular and to regain the ability to get an efficient penile erection and sustain it. In order to effectively treat the condition, the etiology must be identified and treated rather than just the symptoms. (7). Phosphodiesterase type 5 inhibitors (PDE5-Is) are orally active and self-administered drugs for the treatment of ED that are used as needed before sexual intercourse (8). Avanafil (AVA) is a second-generation and highly selective PDE5-I commonly used in the treatment of ED. In 2012, it was approved by the United States Food and Drug Administration (USI-DA), and in the following year, it was approved by the European Medicines Agency (EMA) (9). AVA is subject to significant first-pass metabolism through the human cytochrome P450 enzyme system (8). According to the Biopharmaceutical Classification System (BCS), it is classified as a Class II drug; thus, its dissolution is the rate-limiting step for its absorption, which leads to low oral bioavailability. Also, AVA absorption is altered in the presence of food which delays the time required to reach its maximum serum (9). As a result, modifying AVA's solubility, as well as selecting a different delivery method, may have an impact on bioavailability.

Buccal administration has attracted great attention due to its rapid onset of action and high bioavailability compared to the oral route. This route avoids first-pass metabolism and gastrointestinal tract (GIT) degradation so that it may alleviate possible side effects of the drug (10). The highly vascularized oral mucosa offers a substantial opportunity for the drugs to be absorbed, as they can gain direct access via capillaries and venous drainage to the systemic circulation, circumventing hepatic metabolism. Also, the oral cavity suggests a constant and friendly physiological environment for drug delivery that is maintained by continuous salivary secretion. Moreover, the fluidity of the saliva, low mucin content, absence of proteases, and limited enzymatic activity represent additional advantages for the systemic delivery of drugs after buccal administration (11). Finally, the higher overall permeability of the buccal and sublingual mucosa compared to other mucosae of the mouth is another advantageous characteristic for drug delivery. The oral mucosa is 4-4000 times more permeable than the skin, as water permeation is ten times higher than the skin (12).

Scientific research continues to improve drug delivery across the oral mucosa. Numerous conventional and novel drug delivery systems have been developed for buccal drug delivery. These include; sprays, liquids (solutions or suspensions), semisolids (hydrogels), and solids such as tablets/lozenges (including lyophilized and bio-adhesive) (13), chewing gums, and patches/films. The advances in buccal delivery systems focus on achieving the therapeutic effect by this route, overcoming the challenging environment in the oral cavity, and finding a compromise between patient compliance and clinical benefits. Buccal delivery systems can be designed as a fast, delayed, or controlled delivery of drugs for either local applications or systemic drug delivery (14). The latter is usually aimed at delivering the drug in one of three main ways: rapid release, pulsatile release (with rapid onset followed by a phase where the drug levels are maintained within the therapeutic window), or modified release for an extended period, depending on the addition of different excipients like permeation enhancers or release retardants in the formulations. Sodium deoxycholate is an excellent example of a permeation enhancer that has been shown to increase permeability and, subsequently, systemic delivery, as previously mentioned (15,16).

Additionally, the buccal dosage form's mucoadhesive properties should gain much concern to resist the swallowing action and control the drug release from the buccal mucosa. Mucoadhesive properties can be accomplished using anionic, cationic, and nonionic polymers. Furthermore, stronger mucoadhesive properties have been achieved by using both anionic and cationic polymers, but using anionic polymers can be advantageous due to their lower toxicity (17). Typical examples of anionic mucoadhesive polymers include polyacrylic acid, carbomers, polycarbophil, sodium carboxymethyl cellulose, alginate, and pectin (15). On the other hand, chitosan and hydroxypropyl methylcellulose represent the most widely used cationic and nonionic polymers, respectively (15,18,19).

To sum up, it is of great importance to develop novel strategies that deliver therapeutic substances, through a convenient and/or advanced delivery system, with improved efficacy and bioavailability, reduced dosage frequency and undesirable side effects, improved patient compliance, and commercialization potential.

SUMMARY OF THE INVENTION

As a result, we are investigating a novel approach to develop an AVA dosage form capable of avoiding the hepatic first-pass effect and achieving high therapeutic efficacy. Improving AVA solubility will help accomplish these goals. Therefore, this study aims to develop an optimized buccal tablet formulation loaded with physically modified AVA form, utilizing the suitable carrier, to enhance the drug solubility, bypass hepatic metabolism, and improve the drug bioavailability and efficacy as well as prolong the duration of action. It is worth mentioning that our AVA buccal formulation is the first dosage form for AVA to be administered via the buccal route till the present time. Only five patents (20-24) and nine research articles (5,25-32) revealed different AVA formulations/dosage forms for pharmaceutical applications, but none disclosed a dosage form/formulation for the buccal route of administration.

We embarked on previously disclosed orally disintegrating tablets (ODTs) of AVA [Boman et al. Orally disintegrating dosage form for the administration of AVA, and associated methods of manufacture and use. U.S. Pat. No. 10,028,916 B2, Jul. 24, 2018], which was noticed to be rapidly dissolved/disintegrated in the oral cavity. It also increased the duodenal absorption of AVA. Although ODTs of AVA have a potential enhancement of bioavailability, they are still administered via the oral route without avoiding hepatic metabolism. Therefore, we designed AVA buccal formulations to enhance the bioavailability of AVA and avoid all drawbacks of the oral route, including the extensive hepatic metabolism from the oral route and the consequent repeated daily doses and undesirable side effects. The objective was reflected in enhancing AVA bioavailability and extending the duration over 72 h as displayed by the mean plasma concentration-time profiles (FIG. 8) after oral administration of the optimized buccal tablet on healthy human volunteers (undisclosed in data revealed from ODTs of AVA). Another patent disclosed an in-situ gel loaded with nanoemulsion for encapsulating any phosphodiesterase type V inhibitors for intramuscular administration with expected long duration [Mosli et al. In situ gel loaded with phosphodiesterase type V inhibitors nanoemulsion, US 2015/0099751 A1, Apr. 9, 2015]. However, this patent undisclosed any specific investigations and data regarding AVA encapsulation in the in-situ gel nanoemulsion formulation. The same was found in the patent disclosed a transdermal formulation for the delivery of sildenafil mainly along with the potential delivery of other phosphodiesterase type 5 inhibitors [Fossil et al. Transdermal delivery of sildenafil and other phosphodiesterase type 5 inhibitors, US 2016/0067252 A1, Mar. 10, 2016] and undisclosed any specific investigations or data regarding AVA loading in the transdermal formulation.

Another invention disclosed transfersome-containing transdermal film formulations for enhancing AVA efficacy and bioavailability in rats [El-Say et al. Transfersome-containing transdermal film formulations and methods of use, U.S. Pat. No. 11,185,513 B1, Nov. 30, 2021, Al-hejaili et al. Transdermal film loaded with avanafil ultra-deformable nanovesicles to enhance its percutaneous absorption and bioavailability, AAPS PharmSciTech, 2022 Jan. 4; 23 (0:46]. This invention showed an improved maximum (peak) plasma concentration and area under the curve over 24 h of the transferosomal-transdermal AVA formulation (254.66 ng/mL and 1657.5 ng/mL×h, respectively) compared with the raw AVA transdermal formulation. In addition, one more novel formulation of AVA-loaded invasomal transdermal film [Ahmed et al. Development of an optimized avanafil-loaded invasomal transdermal film. U.S. Pat. No. 10,751,294 B1, Aug. 25, 2020, Ahmed et al. Development of an optimized avanafil-loaded invasomal transdermal film: Ex vivo skin permeation and in vivo evaluation. *Int J Pharm.* 2019; 570:118657] showed an enhanced maximum (peak) plasma concentration of AVA in rats and area under the curve over 24 h (250.39 ng/mL and 1717.04 ng/mL×h, respectively) compared with the raw AVA film. On the other hand, the in-vivo study in human volunteers performed on our AVA buccal formulation disclosed a much higher improvement in AVA bioavailability (FIG. 8) with 314.14 ng/mL and 11044.78 ng/mL×h of maximum (peak) plasma concentration and area under the curve over 72 h, respectively.

Moreover, the plasma concentration of AVA versus the time profile of the AVA buccal formulation reflected the extended duration over 72 h, compared with a maximum of 24 h of other AVA formulations investigated in previous research articles [Alamoudi et al. Investigating the potential of transdermal delivery of avanafil using vitamin e-tpgs based mixed micelles loaded films. *Pharmaceutics* 2021 May 17; 13 (5):739, Kurakula M, Naveen N. R, Patel B, Manne R, Patel DB. Preparation, optimization, and evaluation of chitosan-based avanafil nanocomplex utilizing antioxidants for enhanced neuroprotective effect on PC12 cells. Gels. 2021; 7 (3), Fahmy et al. Development and evaluation of avanafil self-nanoemulsifying drug delivery system with rapid onset of action and enhanced bioavailability. AAPS PharmSciTech. 2015 Feb. 16(1):53-8, Aldawsari et al. Formulation and optimization of avanafil biodegradable polymeric nanoparticles: A single-dose clinical pharmacokinetic evaluation. Pharmaceutics. 2020 Jun. 26; 12 (6):596, Soliman et al. Formulation of avanafil in a solid self-nanoemulsifying drug delivery system for enhanced oral delivery, *Eur J Pharm Sci.* 2016; 93:447-55, Gardouh et al. Mixed Avanafil and Dapoxetine Hydrochloride cyclodextrin nanosponges: Preparation, in-vitro characterization, and bioavailability determination. *J Drug Deliv Sci Technol.* 2022; 68 (December 2021):103100, Kurakula et al. Solid lipid nanoparticles for transdermal delivery of avanafil: optimization, formulation, in-vitro and ex-vivo studies. *J Liposome Res.* 2016; 26 (4):288-96]. To summarize, this confirmed the superiority of our AVA buccal formulation in enhancing AVA bioavailability with prolonged duration over other previously issued patents and research articles.

Figure 1:
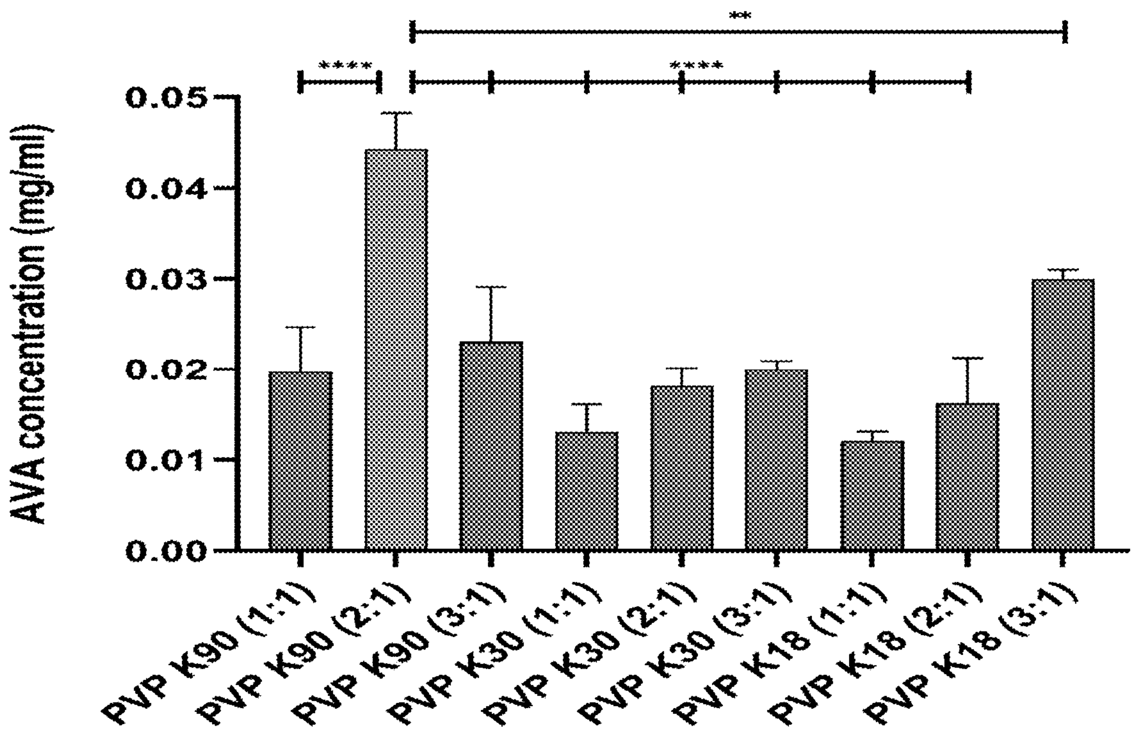
FIG. 1. Solubility of AVA in distilled water after complexation with different PVP polymers (K90, K30, and K18) in different ratios.

* Significant difference at $p<0.05$, Significant difference at $p<0.01$, ** Significant difference at $p<0.0001$.

DESCRIPTION OF THE INVENTION

An aspect of the disclosure provides a buccal formulation of avanafil that demonstrated high bioavailability and prolonged the duration of action, reducing the frequency of dosing and minimizing the side effects potentially beneficial in treating patients with erectile dysfunction. In some embodiments, the solid dispersion of AVA with PVP K90 in the ratio of 2:1 showed the highest solubilization capacity of AVA (0.044 mg/mL). At the same time, the pure drug solubility in distilled water was 0.003 mg/mL.

In another embodiment, converting AVA from crystalline to amorphous form by solid dispersion approach might be the reason behind the high solubilization and/or subsequent adsorption.

In another embodiment, adding the mucoadhesive polymer to the buccal tablet increases its retention time in the oral cavity and controls the drug release from the buccal mucosa.

In another embodiment, incorporating sodium deoxycholate as a permeation enhancer increased the permeability through the buccal mucosa and, subsequently systemic delivery.

In another embodiment, the Design of Experiment (DoE) approach in optimizing the formulation ingredients helped us reach the optimum level of each component that yields the buccal tablet's optimum quality attributes.

In another embodiment, the investigation of the optimized buccal AVA tablet on human volunteers rather than laboratory animals confirmed the results reliability.

In another embodiment, the optimized AVA—buccal tablet improved all the pharmacokinetic parameters compared to the marketed oral tablet.

In other aspects, the optimized buccal AVA tablet significantly increased AVA plasma concentrations over the study period, which indicates the improvement of AVA's relative bioavailability and the prolonged duration of therapeutic action.

Another aspect of the disclosure provides a method of treating male sexual dysfunction in a subject in need thereof, comprising administering a formulation as described herein to the subject.

Methodology

Preparation of AVA—Solid Dispersions

In this study, the polyvinylpyrrolidone polymer was used to enhance the solubility of AVA. Different solid dispersion formulations were prepared using PVP K90, PVP K30, and PVP K18 at three polymer to drug ratios of 1:1, 2:1 and 3:1 (w/w). The known weight (50 mg) of AVA was accurately weighed and dissolved in 5 mL dimethyl sulfoxide (DMSO) to obtain a clear transparent solution. Similarly, each polymer with the specified amount was dissolved in 5 mL methanol separately. The two solutions were mixed and vortexed for 30 min. Subsequently, the mixture was transferred to Büchi-M/HB-140 rotary evaporator (Flawil, St. Gallen, Switzerland) and vacuum dried at 45-50° C. and 22 rpm rotation speed. The dried mass for each AVA—solid dispersion was scrapped, and the obtained AVA—solid dispersion was stored in a desiccator for characterization (33).

Solubility Study of the Elaborated AVA—Solid Dispersions

A solubility study for the prepared solid dispersions was conducted separately in distilled water, as described previously, with full details published (34). In screw-capped vials, 10 mL of distilled water was placed, and an excess amount of either the pure drug or the prepared solid dispersions was added. The vials were kept in a shaking water bath, for 48 h, in a thermostatically controlled shaking water bath (Model 1031; GFL Corporation, Burgwedel, Germany). Samples from the vial were obtained and were determined in triplicate using spectrophotometric assay at $\lambda_{max}$ 285 nm, and the data were expressed as the average ±the standard deviation. The AVA—solid dispersion with the highest water solubility was determined and selected for further investigations.

Powder X-ray Diffraction (PXRD)

The crystallinity of the AVA—solid dispersion with the highest water solubility was investigated using PXRD. Diffractograms for AVA and the selected AVA—solid dispersion were determined using the Ultima IV diffractometer (Rigaku Inc., Tokyo, Japan) (35).

Design of AVA—Buccal Tablet—Formulations

The selected AVA—solid dispersion was incorporated into the design of the AVA—buccal tablet formulations. The Box—Behnken design (BBD) was employed (36-38) to evaluate the effect of the polymer type as $X_1$ (depending on the polymer charge), the polymer percentage as $X_2$, and the mucopenetration enhancer (Sodium deoxycholate) percentage as $X_3$ on the quality attributes of the AVA—buccal tablet—formulations. Fifteen experimental runs were suggested by design. Carbopol as an anionic polymer, HPMC as a nonionic polymer, or chitosan as a cationic polymer were studied as $X_1$. In addition, the level of $X_2$ was investigated from 15 to 25%, while $X_3$ was studied from 1 to 3% (Table 1).

TABLE 1

Box-Behnken design independent levels and dependent variables with the specified responses and assigned goals of AVA-buccal tablet-formulations.

| Independent variables (Factors) | Levels: Low | Medium | High | Units |
|---|---|---|---|---|
| (A) $X_1$: Polymer type | Carbopol (anionic) | HPMC (nonionic) | Chitosan (cationic) | |
| (B) $X_2$: Polymer percentage | 15 | 20 | 25 | (%) |
| (C) $X_3$: Muco-Penetration enhancer percentage | 1 | 2 | 3 | (%) |

| Dependent variables (Responses) | Units | Goal |
|---|---|---|
| $Y_1$: Muco-adhesion strength | G | Maximize |
| $Y_2$: Tablet hardness | N | Maximize |
| $Y_3$: Initial AVA released after 1 h | (%) | Maximize |
| $Y_4$: Cumulative AVA released after 8 h | (%) | Maximize |

Statistical analysis was performed using Statgraphics Centurion 18 software, Statgraphics Technologies, Inc. (Virginia, VA, USA) to investigate the effect of these independent variables on the mucoadhesion strength ($Y_1$), the tablet hardness ($Y_2$), the initial AVA released after 1 h ($Y_3$) and Cumulative AVA released after 8 h ($Y_4$). A lack of fit test was also performed to select the best-fitted model representing responses (39,40).

Elaboration of AVA—Buccal Tablet—Formulations

Fifteen AVA—buccal tablets formulations were prepared, as shown in Table 2 (see below). Each AVA—buccal tablet—formulation contained a specified amount of the selected well-dried AVA—solid dispersion (equivalent to 50 mg AVA), a specified amount of the studied polymer ($X_2$), a predetermined amount of the mucopenetration enhancer (Sodium deoxycholate; $X_3$), 10 mg Fujsil and 4 mg mannitol. The mixture was mixed well with continuous trituration for 10 min in a mortar, and the dried mixture was passed through 20 mesh sieves. The powder excipients were de-lumped individually through a No. 40 mesh sieve. The de-lumped powders were mixed for 15 min Talc powder and magnesium stearate (0.5%) were also de-lumped through the 40-mesh sieve and finally added to the powder blend and mixed for 3 min AVA—buccal tablets were made at 10 KN compression force in a single punch tablet press (Erweka, GmbH, Heusenstamm, Germany) equipped with 9 mm flat round tooling sets (35).

Characterization of the Elaborated AVA—Buccal Tablet—Formulations

The prepared AVA—buccal tablets were visually inspected for any drawbacks during the compression and then examined for their quality attributes, such as weight and content uniformity, thickness, friability, as well as the mucoadhesion strength, tablet hardness, and for the in-vitro release profile of AVA, according to the requirements of the United States Pharmacopeia (41). The drug content of the formulated buccal tablets was determined three times using spectrophotometric assay at $\lambda_{max}$ 285 nm. Twenty tablets (n=20) from each buccal tablet—formulation were weighed using an electronic balance, and their average weight was calculated (initial weight). Then, the tablets were put into the friabilator drum and subjected to 100 revolutions. The tablets were taken, freed from dust, and reweighed (final weight). The friability percentage was calculated from Eq. (1).

$$\text{Friability}(\%) = \frac{\text{Weight}_{initial} - \text{Weight}_{final}}{\text{Weight}_{initial}} \times 100 \quad (1)$$

Mucoadhesion Strength

Mucoadhesion is a characteristic of a dosage form that can interact with mucosal membranes, especially with their mucin component. The mucoadhesive strength measures the force needed to detach the film from the buccal cavity. In this study, the tensile strength method has been utilized to evaluate the mucoadhesive strength of the prepared buccal tablets (42). This method measures the physical interaction between the film and buccal tissue. Results obtained for the mucoadhesive strength using the tensile strength apparatus method were used in the experimental design.

Cow buccal mucosal tissue, obtained from a local slaughter-house, was used as a model to evaluate the mucoadhesive properties for the prepared tablets using Shimadzu Tensile Strength Machine, EZ-SX with high-precision (±0.5%), Shimadzu Co. (Kyoto, Japan). In this experiment, the force required to break the interaction between the prepared tablet and the buccal mucosal tissue was used to assess the mucoadhesive strength (30). A buccal tissue of 2 $cm^2$ was fixed on a glass slide attached to the apparatus lower stage (stationary platform). Samples from each buccal tablet of the same surface area were adhered to another glass slide using two-sided adhesive tape attached to the apparatus upper platform. The tablet was allowed to interact with the mucosal tissue by applying downward force for 2 minutes before running the experiment. The crosshead was then raised at a constant speed of 0.5 mm/min, and the force required for complete detachment (breakpoint) was recorded. Each experiment was repeated three times.

Tablet Hardness

This test investigates a tablet structural integrity and breaking point and how it alters during storage, transportation, packing, and handling conditions before use. A hardness tester is used to study this character. Twenty tablets (n=20) from each buccal tablet formulation were taken and individually placed between the two probes of the hardness tester, one of which is a movable probe and the other is an immovable probe. The force required to break the tablet was recorded, which was taken as the hardness of the tablet (35).

In-vitro Dissolution Study

A USP dissolution test apparatus type II (paddle type), DT 700 LH device, Erweka GmbH DT 700 (Heusen-stamm, Germany) was used to study AVA release from the prepared tablet formulations. Six tablets (n=6) from each formulation were taken and placed individually in a vessel containing 900 mL of phosphate buffer of pH 6.8 with 1% sodium lauryl sulfate to confirm sink condition (43). The test was performed at 37° C.±0.5° C. at a rate of 50 rpm. Samples were diluted with the buffer, filtered via a 0.45 μm Millipore filter (Millipore Corp., Bedford, MA, USA), and analyzed spectrophotometrically at 285 nm, using a UV—Vis spectrophotometer (Jenway 7315, Bibby Scientific Limited, Stone, Staffordshire, UK). Samples of 5 mL were withdrawn at specified time intervals (0.5, 1, 2, 3, 4, 6, and 8 h), and the same volume was replaced with a fresh medium.

Prediction of the Optimized AVA—Buccal Tablet—Formulation

Analysis of variance and multiple response optimization were utilized for predicting the optimized AVA—buccal tablet using the statistical package Statgraphics® Centurion 18 Software (StatPoint, Inc., Warrenton, VA, USA).

Characterization of the Optimized AVA—Buccal Tablet—Formulation

The optimized formulation was prepared and evaluated for the mucoadhesion strength, tablet hardness, and the in-vitro dissolution study (release profile of AVA from the optimized AVA—buccal tablet). This optimized formulation was also characterized via X-ray Diffraction, Fourier Transform Infrared Spectroscopy, and Differential Scanning Calorimetry then scaled up to be evaluated in-vivo for its pharmacokinetic parameters on human volunteers.

Fourier Transform Infrared Spectroscopy (FT-IR)

To investigate any potential interaction between AVA and the studied polymer used to develop the solid dispersion as well as the tablet's excipients in the optimized—buccal tablet—formulation, FT-IR spectra were recorded using a Nicolet iS10, Thermo Scientific Inc. (Waltham, MA, USA) (44).

Differential Scanning Calorimetry (DSC)

DSC was conducted to evaluate AVA's thermotropic characteristics and thermal performance, the selected AVA—solid dispersion, and the optimized AVA—buccal tablet—formulation using a DSC 8000, PerkinElmer, Inc. (Waltham, MA, USA). About 5 mg of the sample was sealed in aluminum pans and heated at the rate of 10° C./min in a temperature range of 25-400° C. under a nitrogen atmosphere at a flow rate of 100 mL/min (45).

In-vivo Pharmacokinetic Evaluation on Healthy Human Volunteers

In this work, an oral pharmacokinetic study was carried out for the optimized AVA—buccal tablet—formulation (test) compared with the marketed tablet (reference) on healthy human volunteers.

Study Design and Conduct

An open-label, single dose, randomized, one-period, parallel design, and one-treatment under fasting conditions comprising fourteen days of screening preceding 24 h study periods were used. The participants were administered a buccal 50 mg dose of AVA from the optimized formulation tablet (test). At the same time, the marketed tablets (reference) were administered the same dose orally with water. The study was carried out at the International Center for Bioavailability, Pharmaceutical, and Clinical Research. (ICBR), Cairo, Egypt. The Institutional Review Board/Independent Ethics Committee (IRB/IEC) at ICBR formally reviewed the objective, design, conduct, and analysis for the proposed study and approved the study protocol on Jul. 18, 2019, with the Ethical Approval Code (RESH-007). The study was accomplished in agreement with the Declaration of Helsinki and the International Conference on Harmonization of Good Clinical Practices. The study was performed following European Medicines Agency (EMA), International Conference on Harmonization (ICH), Good Clinical Practice (GCP), and Food and Drug Administration (FDA) guidelines. Six subjects per group were assigned and gave their written informed consent before participation in this study. The selected subjects were in good health as determined by their comprehensive medical histories, conducting physical examinations, vital signs, and complete laboratory investigations (hematology, biochemistry, and urine analysis). They were also screened for viral infections and remained under close medical supervision before, during, and after the study period. Each subject fasted for at least 12 h before administering the studied tablets. Subjects were kept in-house for 72 h before and after administration of the drug so that regular blood sampling could be withdrawn at a predetermined time (as described in the Blood Sampling section).

Subjects

Twelve healthy Egyptian male volunteers participated in the study. The subjects' age and body mass index (BMI) ranged from 21 to 30 years and 20 to 30 $kg/m^2$, respectively. Their median height was 172±5.3 cm. Subjects were classified into two groups (6 per group); the first group was administered the optimized AVA—buccal tablet, and the second group was given the oral commercial tablets, namely; Stendra®, Metuchen Pharmaceuticals, LLC (Freehold, NJ, USA).

Blood Sampling 5 mL blood samples were taken and collected in heparinized tubes before and 0.08, 0.25, 0.5, 0.75, 1, 1.25, 1.5, 2, 3, 4, 6, 8, 10, 12, 24, 48, and 72 h following oral administration of the test and reference tablets. The collected samples were centrifuged at 3000 rpm for 5 min, and the plasma samples were collected and stored at −20° C. until analysis.

Chromatographic Conditions

A high-performance liquid chromatography (HPLC) method was developed at Egyptian Research and Development Company laboratories to analyze AVA in human plasma. The method was validated according to the FDA Bio-analytical Method Validation Guidelines 2003 (29). The linearity of the method was studied within the concentration range of 10-600 ng/mL, with a regression coefficient ($R^2$) =0.998. Azithromycin was used as an internal standard. The obtained results for method validation were within the acceptance criteria as indicated in the recommended guidelines. The described method proved to be sensitive, accurate and reproducible, with a lower limit of AVA quantification of 10 ng/mL. The HPLC-MS/MS-system consisted of Agilent series 1200 of Agilent Technologies Inc. (Santa Clara, California, USA). The system is equipped with a quaternary pump (G1311A), an autosampler (G1329A), a vacuum degasser (G1322A), and an ESI electrospray ionization ion source. Mass Hunter software was used. The mobile phase consisted of acetonitrile 50% and ammonium formate 10 mmole 50%. The flow rate was adjusted at 1 mL/min A reverse phase Intersil ODS-3 (4.6 mm×50 cm, dp 5 μm) column of GL Sciences (Tokyo, Japan) was used at 25° C.

Pharmacokinetic Data Analysis

A non-compartmental pharmacokinetic model using PKsolver (An add-in program for pharmacokinetic data) was used to calculate the pharmacokinetic parameters of AVA. Maximum (peak) plasma concentration over the time specified ($C_{max}$), time point to reach the maximum plasma concentration ($T_{max}$), and the area under the plasma concentration-time curve from zero time to the last measurable concentration ($AUC_{0-t}$) were calculated by the linear trapezoidal method. In addition, individual estimates were made of the terminal elimination rate constant ($K_{el}$), the mean residence time ($MRT_{0-\infty}$), which was calculated by the ratio of AUMC to AUC, and the elimination half-life ($t^{1/2}{}_{/2}$), which was calculated as $0.693/K_{el}$. Moreover, the apparent total body clearance of the drug after oral administration (C1) was calculated by dividing the dose by AUC, and the apparent volume of distribution during the terminal phase after non-intravenous administration ($V_d$) was calculated by multiplying total body clearance by MRT. Finally, the relative bioavailability of the optimized AVA—buccal tablet ($AUC_{test}/AUC_{reference}\times100$) was determined (46).

Statistical Analysis

GraphPad Prism, version 8.4.2 Software (San Diego, CA, USA) was used to analyze all the obtained data statistically. The solubility study analysis was made using a one-way ANOVA/Tukey—Kramer post-hoc test at $P<0.05$, and data are expressed as mean±SD. Regarding the plasma concentration-time curve, two-way ANOVA followed by Sidak' s multiple comparisons test was conducted to compare each mean with the others at each time point and assess the significance between groups. At the same time, a two-tailed unpaired t-test was used to assess the pharmacokinetic parameters of the formulations. Results with $P<0.05$ were considered significant.

Results and Discussion

Solubility Study of the Elaborated AVA—Solid Dispersions

The selection of PVP polymers for enhancing AVA solubility was based on the previously confirmed reports for the superiority of these polymers, which particularly improved AVA solubility (36). FIG. 1 illustrates the solubility of AVA in distilled water after complexation with different PVP polymers (K90, K30, and K18) in different ratios. PVP K90: AVA with the ratio 2:1 showed the highest solubilization capacity of AVA (0.044 mg/mL), while the pure drug solubility in distilled water was 0.003 mg/mL, which confirms that AVA is practically insoluble in water according to USP, which describes the substance that needs more than 10,000 mL to dissolve 1 g with the practically insoluble one. It is also noted that PVP K90: AVA—solid dispersion (2:1) significantly increased AVA solubility with a 0.0033 P-value over PVP K18: AVA—solid dispersion (3:1) and with P-value<0.0001 over all other ratios and other types of used polymers as well (FIG. 1).

Powder X-ray Diffraction (PXRD)

Figure 2:
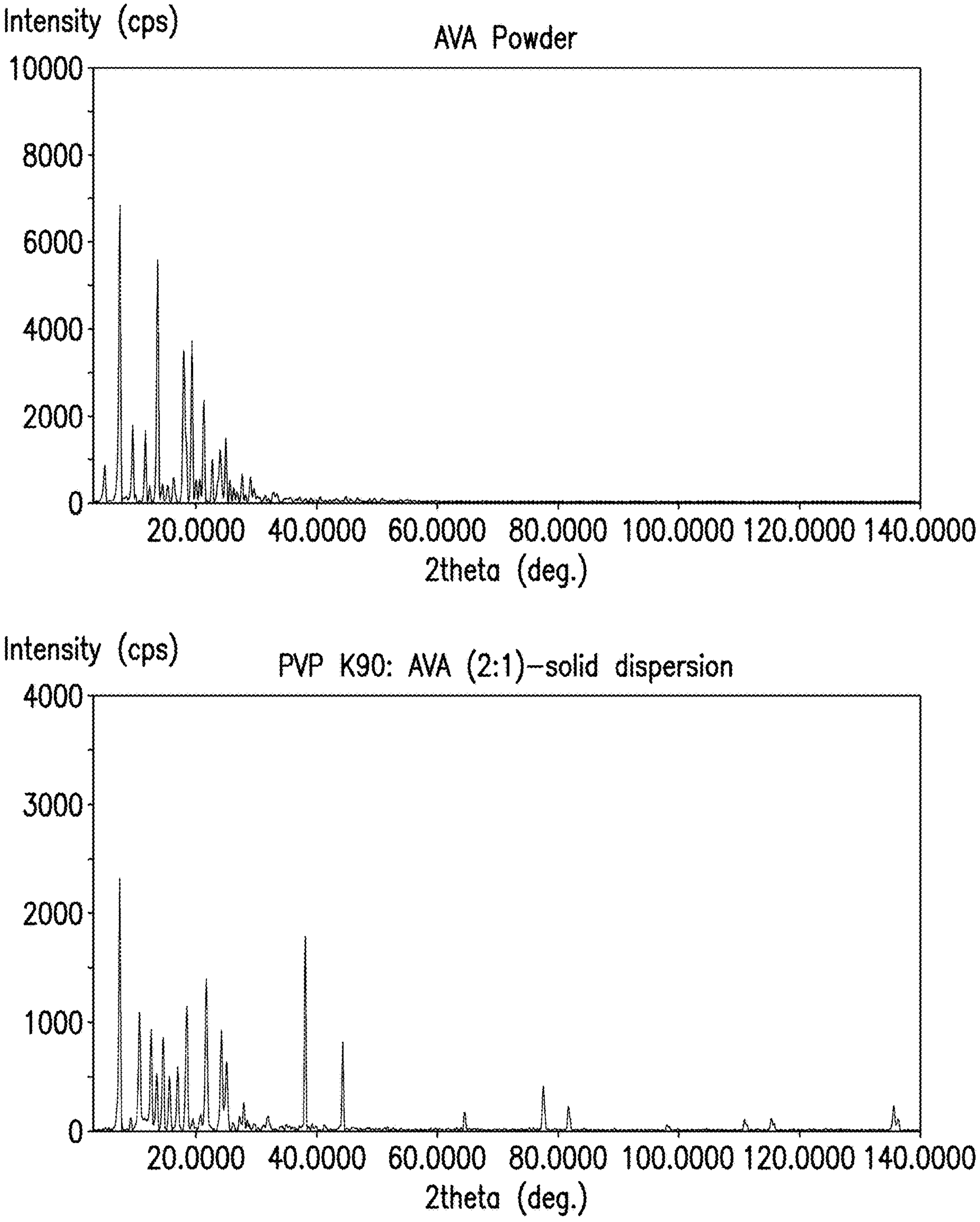
FIG. 2. Powder X-ray diffraction patterns of pure avanafil (top panel), and its solid dispersion with PVP K-90 (1:2 ratio)(bottom panel).

PXRD was used to determine the crystalline state of AVA in its pure state and PVP K90: AVA (2:1)—solid dispersion. It measures the disappearance of constructive, specific peaks of drugs in the solid dispersion and retaining peaks of the polymer material. The PXRD pattern in FIG. 2 of the pure drug (AVA) shows sharp diffraction peaks at 7.3, 13.6, 17.9, 19.3, and 21.3° with high intensity, which indicates that the pure drug was present in the crystalline state. The decrease in the number and intensity of the characteristic peaks in the XRD pattern of the solid dispersion, as illustrated in FIG. 2, indicates the conversion of AVA from crystalline to amorphous form. This lack of crystallinity in the formulation might be due to AVA solubilization and/or subsequent adsorption on the studied PVP K90 polymer (47,48). The solubilization or amorphization of the drug in the solid dispersion leads to the resulting improvement in the apparent solubility that has been confirmed in the previous section. Consequently, PVP K90: AVA (2:1)—solid dispersion has been selected for further inclusion in the buccal tablet formulation design.

Formulation and Evaluation of the AVA—Buccal Tablet—Formulations

Fifteen AVA—buccal tablet—formulations were prepared as suggested by BBD (Table 2). Quality control tests of the prepared AVA—buccal tablet—formulations revealed that the AVA content of all formulations was found to be in the range of 85.58% to 113.26% in F14 and F1, respectively. These results were compiled with USP's official specifications and reflected the weight uniformity in all formulations (41). In addition, there is no observed variation in the thickness of all formulations. The friability and the hardness of all tablet formulations ranged from 0.01-0.062%, and 96.67-167 N, respectively, which complied with BP friability test limits (<1%). The friability and hardness results reflected the prepared buccal tablets' acceptable mechanical properties and good breaking strength. Moreover, the mucoadhesion strength of the prepared AVA—buccal tablet—formulations was found to be from 129.21 to 351.85 Gin F-6 and F-4, respectively. From the in-vitro dissolution study (FIG. 3), the percentages of initial release were varied from 4.843% for F12 to 12.173% for F1, while the percentages of cumulative release were ranged from 83.005% for F12 to 110.71% for F. In the following sections, full analysis and elucidations regarding the selected quality attributes and the optimized formulation's prediction will be discussed in detail and thoroughly.

Response Surface Methodology for Optimization of the Formulations

RSM has been widely used in the formulation development of modern products and for modifying existing products. It produces polynomial equations and maps the responses over formulation variables to determine the optimum formulation (49). This study utilized the RSM to recognize the influence of the dependent variables ($X_1$, $X_2$, and $X_3$) on the studied response variables ($Y_1$, $Y_2$, $Y_3$, and $Y_4$). Table 2 lists the BBD matrix that involves all suggested formulations' independent and dependent variables.

TABLE 2

Composition of Box-Behnken design for AVA-buccal tablet-formulations and observed values of the studied responses.

| | Factors | | | Responses** | | | |
|---|---|---|---|---|---|---|---|
| Formulations* | $X_1$ | $X_2$ (%) | $X_3$ (%) | $Y_1$ G | $Y_2$ N | $Y_3$ (%) | $Y_4$ (%) |
| F1 | HPMC | 15.0 | 3.0 | 207.54 | 116.33 | 12.173 | 110.71 |
| F2 | HPMC | 25.0 | 1.0 | 152.24 | 160 | 9.207 | 95.809 |
| F3 | HPMC | 25.0 | 3.0 | 333.23 | 167 | 10.108 | 101.492 |
| F4 | Carbopol | 15.0 | 2.0 | 351.85 | 114 | 9.684 | 98.737 |
| F5 | Chitosan | 20.0 | 1.0 | 202.45 | 125.33 | 10.001 | 99.959 |
| F6 | Carbopol | 20.0 | 1.0 | 129.21 | 103 | 5.068 | 85.906 |
| F7 | Chitosan | 25.0 | 2.0 | 271.66 | 134 | 7.119 | 86.183 |
| F8 | Chitosan | 20.0 | 3.0 | 217.84 | 127.33 | 8.873 | 96.204 |
| F9 | Chitosan | 15.0 | 2.0 | 323.14 | 106.33 | 7.552 | 96.716 |
| F10 | Carbopol | 20.0 | 3.0 | 254.74 | 117.33 | 9.932 | 99.753 |
| F11 | HPMC | 15.0 | 1.0 | 316.51 | 96.67 | 8.086 | 98.804 |
| F12 | Carbopol | 25.0 | 2.0 | 256.58 | 136.33 | 4.843 | 83.005 |
| F13 | HPMC | 20.0 | 2.0 | 245.82 | 146 | 7.212 | 92.149 |
| F14 | HPMC | 20.0 | 2.0 | 286.54 | 141 | 6.523 | 94.369 |
| F15 | HPMC | 20.0 | 2.0 | 247.50 | 148.33 | 7.362 | 93.661 |

*Each 200 mg AVA-buccal tablet-formulation contains 150 mg PVP-K90: AVA-solid dispersion (2:1), specified amount of selected polymer ($X_2$), specified amount of muco-penetration enhancer (Sodium deoxycholate; $X_3$), 10 mg Fujsil and 4 mg Mannitol.
**Values of responses are the means of triplicate measurements for each response and SD values did not exceed 5% of the stated values.

The mucoadhesion strength, tablet hardness, and the in-vitro dissolution profile (the selected quality attributes as dependent variables/responses) were investigated using a 3-factor, 3-level BBD model. This model was employed to inspect, augment, and evaluate the quadratic and interaction effects of the selected factors on the responses. In addition, polynomial equations and a lack of fit test summary data were generated and discussed in the following sections.

Lack of Fit Test

The lack of fit test is premeditated to reveal the suitability of the selected model to demonstrate and represent the detected data. In the case of the P-value for lack of fit in the ANOVA results that is more than or equal to 0.05, the model seems suitable for the detected data at the 95.0% confidence level (50,51). The lack of fit test summary data that is displayed in Table 3 revealed that the selected model for all responses has an insignificant lack of fit (all P-values are more than 0.05).

TABLE 3

| Parameters of lack-of-fit tests of responses. | | | | | |
|---|---|---|---|---|---|
| | Lack-of-fit parameters | | | | |
| Responses | Sum of Squares | Degree of Freedom | Mean Square | F-ratio | Lack of Fit p-value |
| $Y_1$ | 2368.01 | 3 | 789.338 | 1.49 | 0.4263 |
| $Y_2$ | 749.317 | 3 | 249.772 | 17.81 | 0.0536 |
| $Y_3$ | 4.27866 | 3 | 1.42622 | 7.12 | 0.1256 |
| $Y_4$ | 42.6288 | 3 | 14.2096 | 11.05 | 0.0841 |

Consequently, and according to these findings, the Quadratic model selected to represent the observed data can be considered a suitable model for all responses utilized in the design of experiment conducted in this research work.

Quantitative Estimation of Factors' Effect

The relevancy-oriented mathematical treatment among the selected factors and the detected responses were expressed as polynomial equations and explained for their significance by ANOVA. The estimated factors' effects and the corresponding P-values obtained from ANOVA for all the studied responses are represented in Table 4.

TABLE 4

| Estimated effects of factors and associated P-values for the responses of AVA-buccal tablet-formulations. | | | | | | | | | | |
|---|---|---|---|---|---|---|---|---|---|---|
| | | Factors | | | | | | | | |
| | | $X_1$ | $X_2$ | $X_3$ | $X_1^2$ | $X_1X_2$ | $X_1X_3$ | $X_2^2$ | $X_2X_3$ | $X_3^2$ |
| $Y_1$ | Factor effect | 5.68 | −46.33 | 53.237 | −10.476 | 21.896 | −55.071 | 92.175 | 144.98 | −107.321 |
| | p-values | 0.76 | 0.1046 | 0.0823 | 0.7049 | 0.4423 | 0.1394 | 0.0615 | 0.0243* | 0.0465* |
| $Y_2$ | Factor effect | 5.583 | 41 | 10.748 | −39.198 | 2.67 | −6.165 | −5.693 | −6.33 | −14.528 |
| | p-values | 0.1696 | 0.0041* | 0.0557 | 0.0097* | 0.5499 | 0.2415 | 0.282 | 0.2331 | 0.0651 |
| $Y_3$ | Factor effect | 1.0045 | −1.5545 | 2.181 | −1.15783 | 2.204 | −2.996 | 1.69217 | −1.593 | 4.03017 |
| | p-values | 0.0865 | 0.039* | 0.0204* | 0.1308 | 0.0388* | 0.0216* | 0.0681 | 0.0706 | 0.0131* |
| $Y_4$ | Factor effect | 2.91525 | −9.6195 | 6.92025 | −8.481 | 2.5995 | −8.801 | 4.0155 | −3.1115 | 12.606 |
| | p-values | 0.068 | 0.0069* | 0.0132* | 0.0188* | 0.1489 | 0.0162* | 0.0766 | 0.1111 | 0.0087* |

$X_1$ is the Polymer type, $X_2$ is the Polymer percentage (%), X3 is the Muco-Penetration enhancer percentage (%), $X_1X_2$, $X_1X_3$, $X_2X_3$ are the interaction terms between the factors, $X_1^2$, $X_2^2$, $X_2^3$ are the quadratic terms of the factors, $Y_1$ is the Muco-adhesion strength (G), $Y_2$ is the Tablet hardness (N), $Y_3$ is the Initial AVA released after 1 h (%), and $Y_4$ is the cumulative AVA released after 8 h (%).

*Significant effect of factors on individual responses.

The effectiveness of any factor will be considered significant in case the effect value is more than zero and its P-value is not equal to or more than 0.05. Besides, the synergistic factor effect will be labeled with a positive sign, whereas a negative sign symbolizes the antagonistic effect.

According to the given outcomes, the percentage of the polymer used to develop the buccal tablets formulation ($X_2$) was found to significantly influence the tablet hardness ($Y_2$) synergistically at a P-value of 0.0041. $X_2$ was also found to significantly and antagonistically affect the initial and cumulative amount of AVA released after 1 h ($Y_3$) and 8 h ($Y_4$) at P-values of 0.039 and 0.0069, respectively. The percentage of mucopenetration enhancer ($X_3$) was significantly influenced by $Y_3$ (P-value of 0.0204) and $Y_4$ (P-value of 0.0132). Although the type/charge of polymer ($X_1$) was found to exhibit a non-significant effect on all responses, it was noted that the quadratic effect of $X_1$ ($X_1^2$) negatively influenced both $Y_2$ and $Y_4$ with P-values of 0.0097 and 0.0188, respectively. Furthermore, $Y_3$ was influenced synergistically (P=0.0388) by the interaction term ($X_1X_2$), while the interaction term ($X_1X_3$) had an antagonistic effect on both $Y_3$ and $Y_4$ (0.0216 and 0.0162 P-values, respectively). In addition, it was noted that the quadratic term of $X_3$ ($X_3^2$) had a noticeable negative effect on the mucoadhesion strength (Y1) with a P-value of 0.0465, and a positive effect on $Y_3$ and $Y_4$ at P-values of 0.0131 and 0.0087, respectively. In addition, a significant agonistic effect on $Y_1$ (P=0.0243) was exhibited by the interaction term ($X_2X_3$). The quadratic term of $X_2$ ($X_2^2$) was found to have no significant effects on any of the studied responses (Table 4).

Effect of the Independent Variables on Mucoadhesion Strength ($Y_1$)

The mucoadhesion strength test was performed to measure the ability of the prepared buccal tablets to interact with the buccal epithelial cells, which in turn plays an important role in the formulation absorptivity and bioavailability. Carbopol, chitosan, and HPMC have been verified for their efficacy as mucoadhesive polymers in pharmaceutical research (52-54).

From the data presented in Table 4, the mucoadhesion strength ($Y_1$) was found to range from 129.21-351.85 G in F-6 and F-4, respectively. $Y_1$ was positively influenced by the interaction term of $X_2$ and $X_3$ ($X_2X_3$) and negatively influenced by the quadratic term of $X_3$ ($X_3^2$). The Pareto chart and contour response surface plot of $Y_1$ (FIGS. 4 and 5) also confirmed this finding. As demonstrated in F1 and F3, at fixed levels of $X_1$ and $X_3$ (HPMC buccal tablets with 3% sodium deoxycholate; high level of mucopenetration enhancer), the increase in $X_2$ from 15 to 25% was accompanied by an increase in $Y_1$ from 207.54 to 333.23 G. Also, the increase in $X_3$ from 1 to 3% in F6 and F10 resulted in an increase in $Y_1$ from 129.21 to 254.74 G at constant levels of $X_1$ and $X_2$ (20% Carbopol buccal tablets). To better describe this complex interaction, the increase in $X_2$ at high levels of $X_3$ will result in an increase in $Y_1$. Also, the increase in $X_3$ at mid-high levels of $X_2$ will increase $Y_1$. The interaction between the polymer used and sodium deoxycholate, used as a mucopenetration enhancer, was found to depend on different properties such as; the charge of the polymer, the number of sites available for binding with sodium deoxycholate, and the hydrophilic/hydrophobic characteristics of the studied polymer (55,56). This complexation is well-known and directly related to the intricate mutual effect of $X_2$ and $X_3$ on the mucoadhesion property of tablets.

Effect of the Independent Variables on the Tablet Hardness ($Y_2$)

Hardness is a crucial test that is used to evaluate the mechanical durability of formulated tablets. Table 2 shows the results of the hardness for the prepared buccal tablets. The results ranged from 96.67 to 167 N for F11 and F3, respectively.

Figure 4:
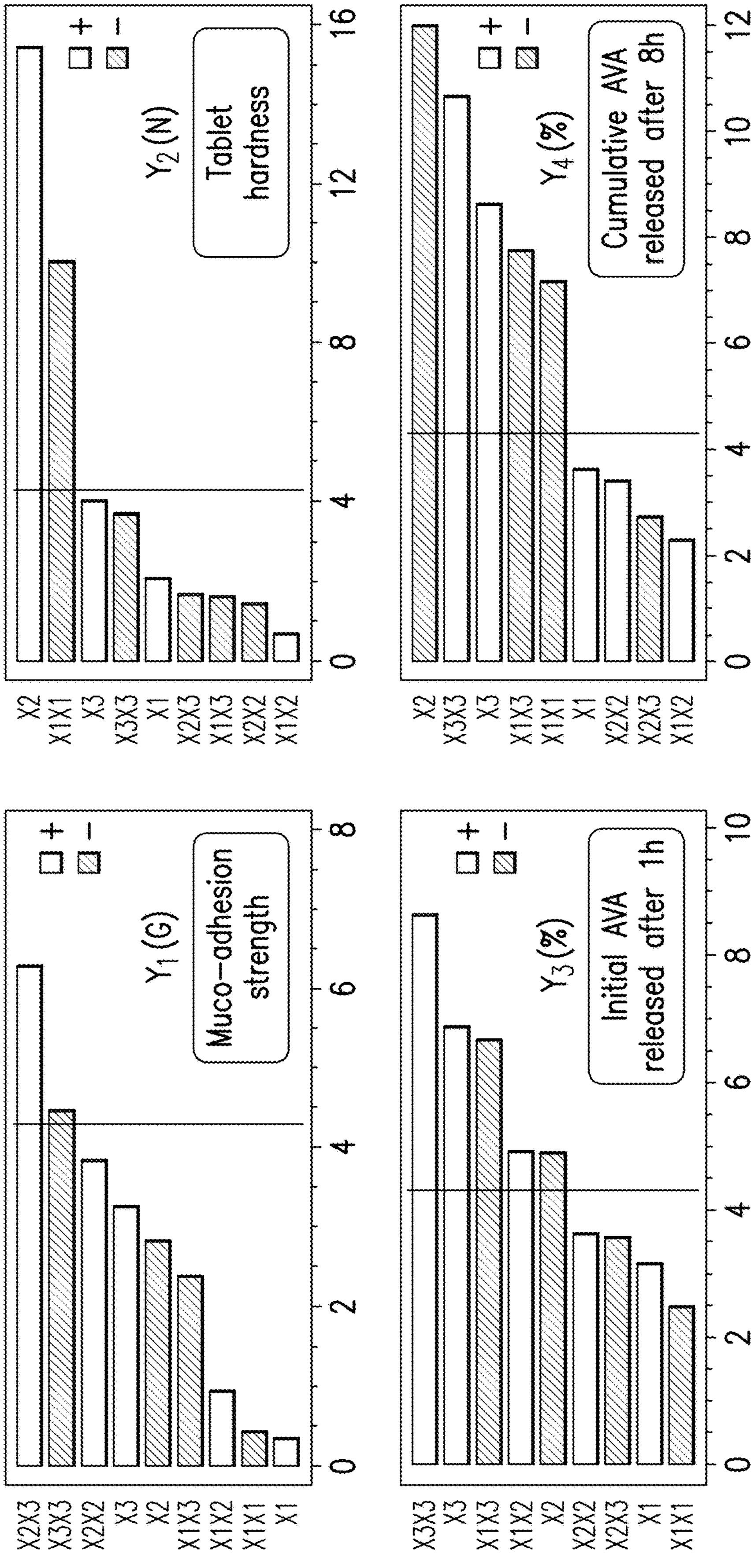
FIG. 4. Pareto charts of all independent variables on mucoadhesion strength, tablet hardness, initial AVA released after 1 h, and cumulative AVA released after 8 h.
Figure 5:
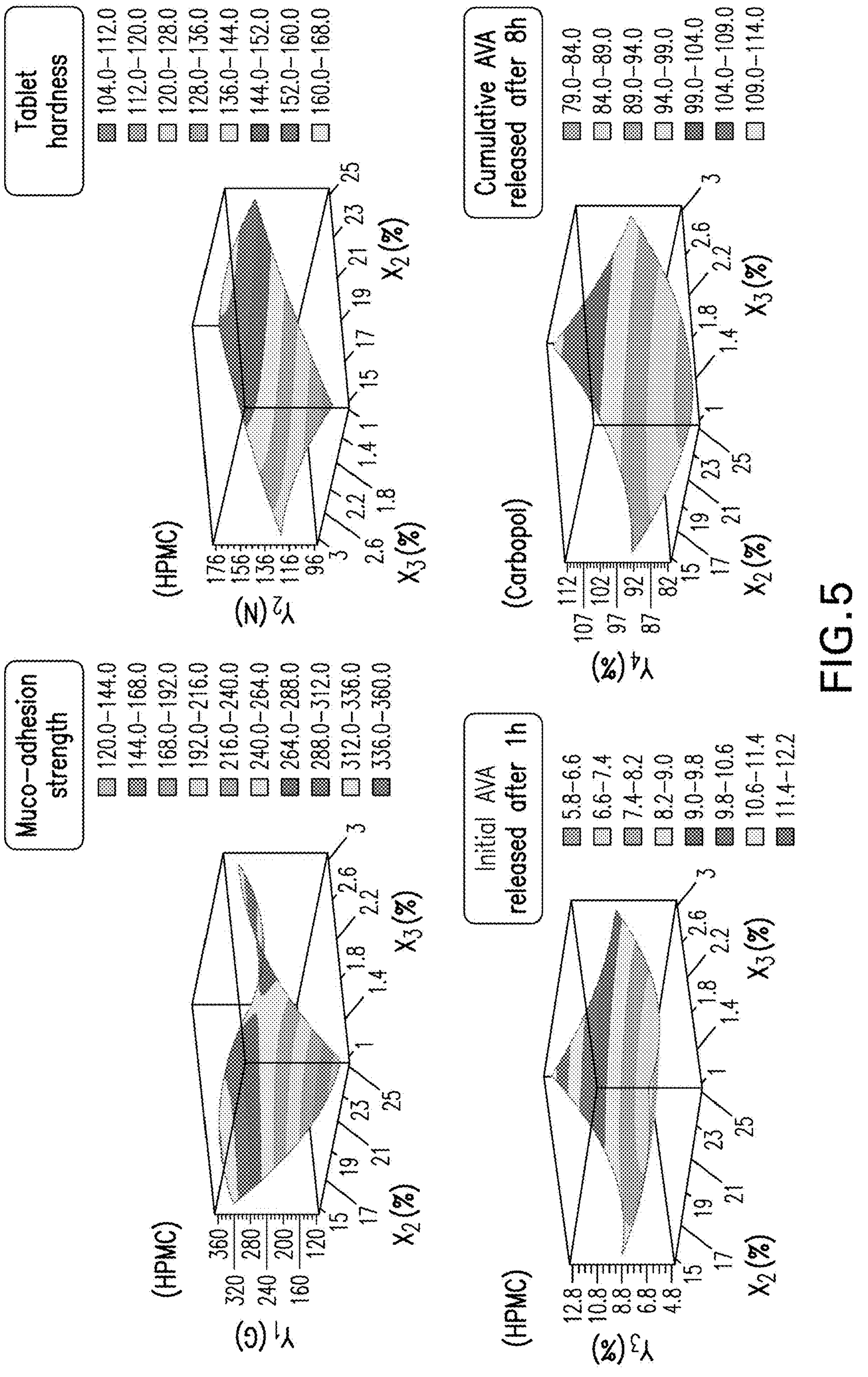
FIG. 5. Estimated three-dimensional response surface plots for the effect of the studied variables on mucoadhesion strength, tablet hardness, initial AVA released after 1 h, and cumulative AVA released after 8 h.

The estimated effects of factors and the associated p-values are displayed in Table 4, while FIGS. 4 and 5 demonstrate the Pareto chart and contour response surface plot of $Y_2$. ANOVA results exposed that the tablet hardness ($Y_2$) was highly influenced by the polymer percentage ($X_2$) with a p-value of 0.0041. As the $X_2$ was increased from 15 to 25% at the same level as the other factors, the hardness was increased from 96.67 to 160 N in F11 and F2, respectively, and from 106.33 to 134 n in F9 and F7, respectively, which an indication of the synergistic effect of $X_2$ on $Y_2$. This trend was also confirmed by the decrease in the hardness from 136.33 to 114 in F12 and F4, respectively, as $X_2$ decreased from 25 to 15%. This effect is expected since all the studied polymers that have been utilized in buccal tablets' formulations have been used as binders in tablet manufacturing (57-60). Therefore, increasing the concentration of these polymers will lead to an increase in tablet hardness. On the other hand, the quadratic term of $X_1$ ($X_1^2$) also had a negative influence on $Y_2$.

Influences of the Independent Variables on AVA Release ($Y_3$ and $Y_4$)

Figure 3:
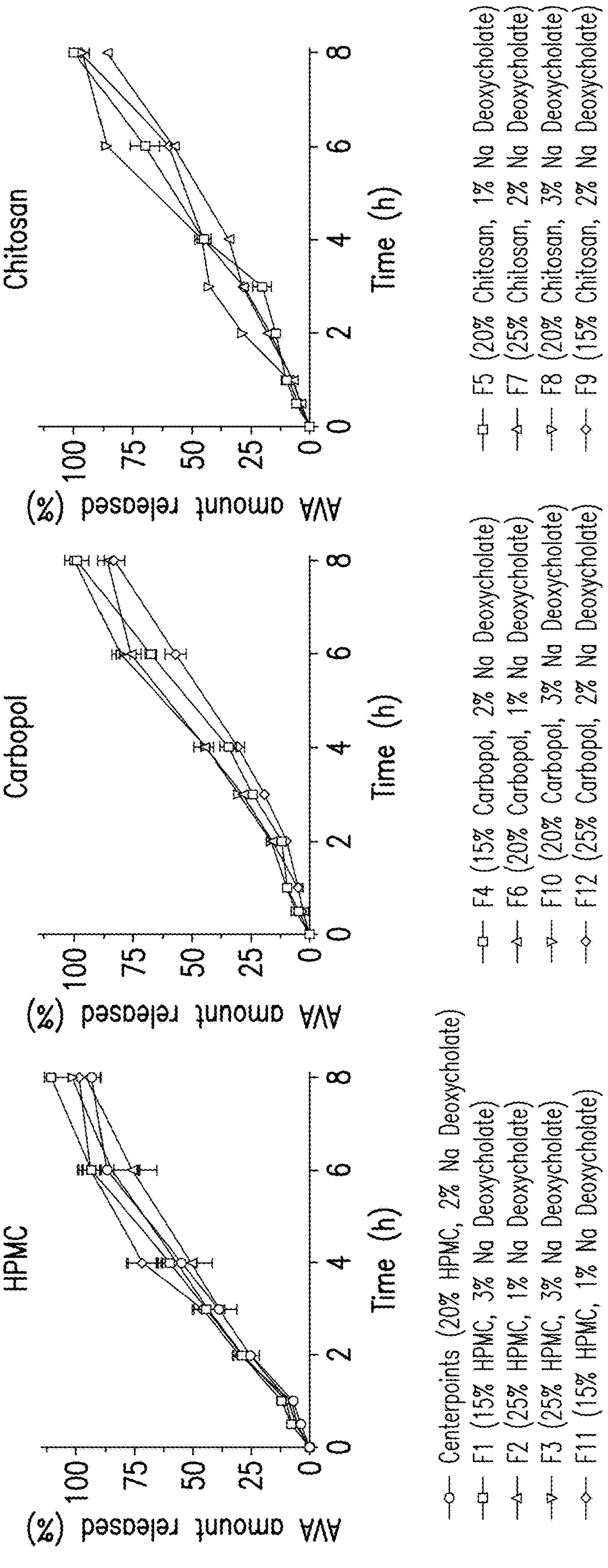
FIG. 3. In-vitro dissolution profiles of AVA from different buccal formulations.

In this study, the initial percentage of drug release after 1 h ($Y_3$) and the cumulative percentage of drug release after 8 h ($Y_4$) were studied after investigation of the drug in vitro release profile displayed in Table 2 and FIG. 3. The highest initial and cumulative AVA released was obtained from the HPMC-based buccal tablet namely; F1 (12.173% and 110.71%, respectively), while the lowest initial and cumulative AVA released was observed from the Carbopol-based buccal tablet namely; F12 (4.843% and 83.005%, respectively). It was also noted that F3 "HPMC-based buccal tablet" ranked second in the highest initial and cumulative AVA release (10.108% and 101.492%, respectively). The second lowest initial and cumulative AVA released was obtained from F6 "Carbopol-based buccal tablet" (5.068% and 85.906%, respectively). In general, HPMC-based buccal tablets illustrated superiority in their drug release compared to the other polymer-based buccal tablets. Data represented in Table 4 and the graphical illustration of the Pareto chart and contour response surface plot for $Y_3$ and $Y_4$ (FIGS. 4 and 5) revealed that the type of polymer ($X_1$) did not have a significant effect on the release profile of AVA. In addition, the polymer percentage ($X_2$) was found to have a significant antagonistic effect on $Y_3$ and $Y_4$. According to the data obtained for F9 and F7, the increase in polymer percentage from 15 to 25% was accompanied by a decrease in the initial release percentage from 7.552% to 7.119%, respectively. The cumulative drug release percentage decreased from 96.716% to 86.183%, respectively, at the same levels of $X_1$ and $X_3$. Furthermore, it was also noticed that the percentage of mucopenetration enhancer ($X_3$) had a significant synergistic effect on both $Y_3$ and $Y_4$. Both F1 and F3 were elaborated with 3% sodium deoxycholate (highest $X_3$ value), which is reasonable to exhibit the maximum release profiles in such formulations. On the other hand, carbopol-based buccal tablets demonstrated the lowest drug release profile, the effect that may be attributed to the carbopol-PVP interpolymer complexation that potentially resulted in achieving slower drug release (61), especially with the comparatively mid-level of the mucopenetration enhancer percentage. Moreover, the antagonistic effect of the interaction term ($X_1X_3$) and the synergistic effect of the quadratic term of $X_3$ ($X_3^2$) were also found to significantly influence $Y_3$ and $Y_4$.

Statistical Analysis and Mathematical Modeling of the Experimental Data

After investigating and analyzing the influences of the studied independent variables on the selected responses, mathematical modeling for each response was generated. The best-fit method developed the following equations (Eqs. 2-5) that describe the analysis outcomes of the multiple linear regression.

Mucoadhesion strength ($Y_1$)

$$=1402.06+14.12X_1-107.37X_2-48.7X_3-5.24X_1^2+2.19X_1X_2-27.54X_1X_3+1.84X_2^2+14.498X_2X_3-53.66X_3^3 \quad (2)$$

Tablet hardness ($Y_2$)

$$=-47.55+3.62X_1+9.92X_2+47.09X_3-19.599X_2^2+0.267X_1X_2-3.08\,X_1X_3-0.114X_2^2-0.633X_2X_3-7.264X_3^2 \quad (3)$$

Initial AVA released after 1 h ($Y_3$)

$$=23.186-0.91X_1-1.19X_2-3.78X_3-0.579X_1^2+0.22X_1X_2-1.498X_1X_3+0.034X_2^2\mu-0.159X_2X_3+2.015X_3^2 \quad (4)$$

Cumulative AVA released after 8 h ($Y_4$)

$$=150.602+5.06X_1-3.55X_2-15.53X_3-4.24X_1^2+0.26X_1X_2-4.4X_1X_3+0.08X_2^2-0.31X_2X_3+6.3X_3^2 \quad (5)$$

Elaboration and Characterization of the Optimized AVA-buccal Tablet-Formulation Multiple response optimization produces an optimized AVA-buccal tablet-formulation that achieves the study goal. The optimized parameters were anticipated and investigated to compromise amongst responses to get a combination of factors' levels that intensify the desirability function over the study goals (62). The optimized levels of independent factors were identified, and the optimum formulation was found to have HPMC as the optimum polymer type, 25% and 3% of $X_1$, $X_2$, and $X_3$, respectively. The optimized AVA—buccal tablet— formulation with 0.726optimum desirability value was prepared and assessed as previously illustrated in the earlier section. The observed values for $Y_1$, $Y_2$, $Y_3$, and $Y_4$ were 347.33 G, 166.8 N, 11.98%, and 99.67%, respectively, while the predicted values of these responses were 329.5 G, 157.463 N, 9.396%, and 98.911%, respectively.

Fourier-Transform Infrared Spectroscopy

Figure 6:
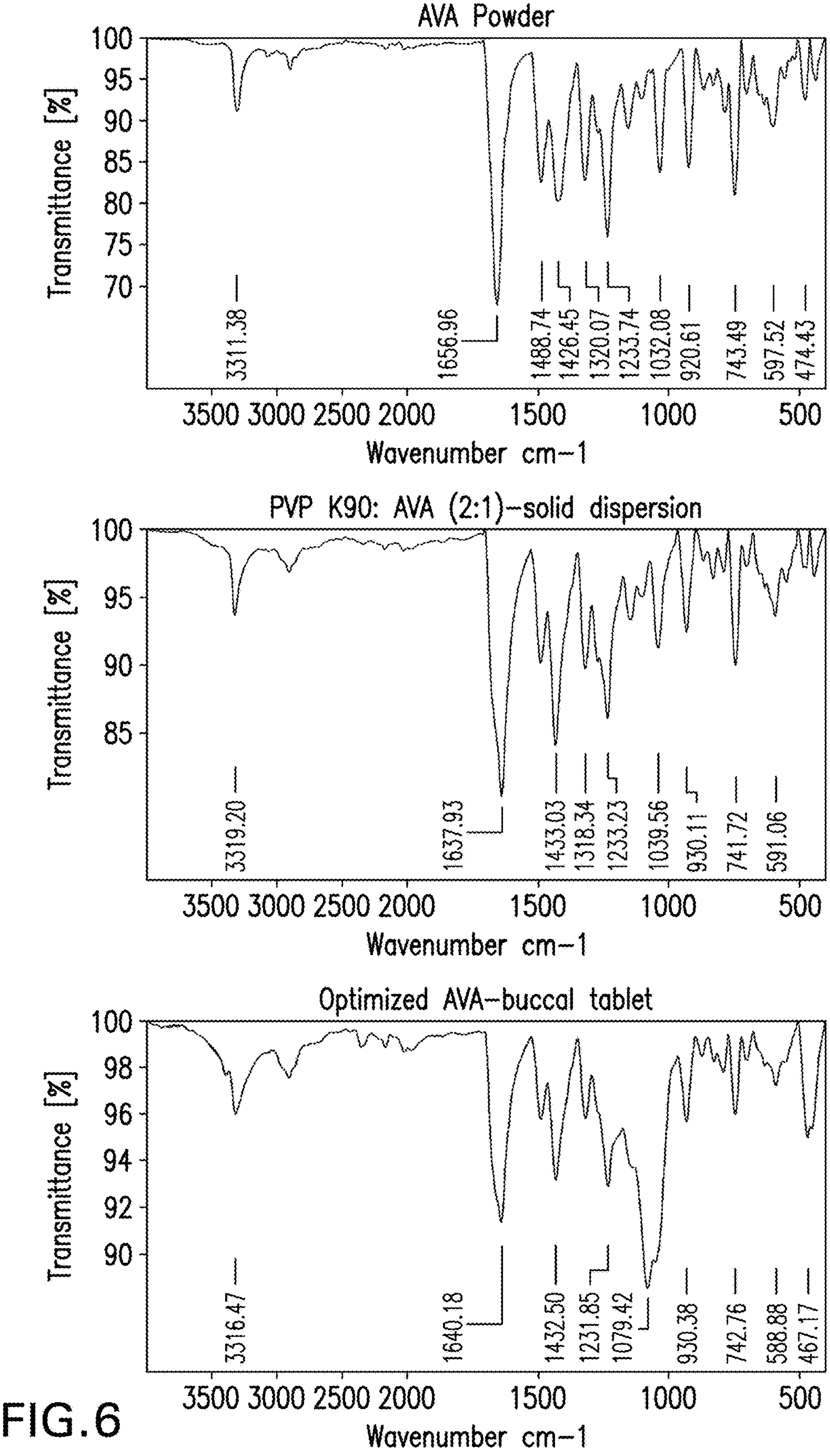
FIG. 6. FTIR Spectra of pure avanafil (top panel), avanafil solid dispersion with PVP K-90 (2:1 ratio) (middle panel), and the optimized buccal tablet (bottom panel).

FIG. 6 shows the FTIR spectra of raw AVA powder, PVP K90: AVA (2:1)—solid dispersion, and the optimized AVA—buccal tablet—formulation. Absorption peaks properties for AVA were recorded in the 1700-450 $cm^{-1}$ range. This spectral range contains 1656 to 740 $cm^{-1}$ domains, which is important for finding AVA analog. A specific AVA absorption band was observed at 1657 $cm^{-1}$, which is attributed to the carbonyl group of the amide bond (HN—C═O). Another drug peak was detected at 1435 $cm^{-1}$, related to the stretching vibration of the C—N and a band at 743 $cm^{-1}$ represent the benzene (63). It is also observed from FIG. 6 that the absorption bands of both PVP K90: AVA (2:1)—solid dispersion and the optimized AVA— buccal tablet—formulation did not show interference with the characteristic drug peaks, indicating the absence of chemical interaction between the drug and the components used to develop both formulations (solid dispersion and the studied tablet). The following section will explain more explanation for the interaction between AVA and the studied components in the two formulations (DSC).

Differential Scanning Calorimetry

Figure 7:
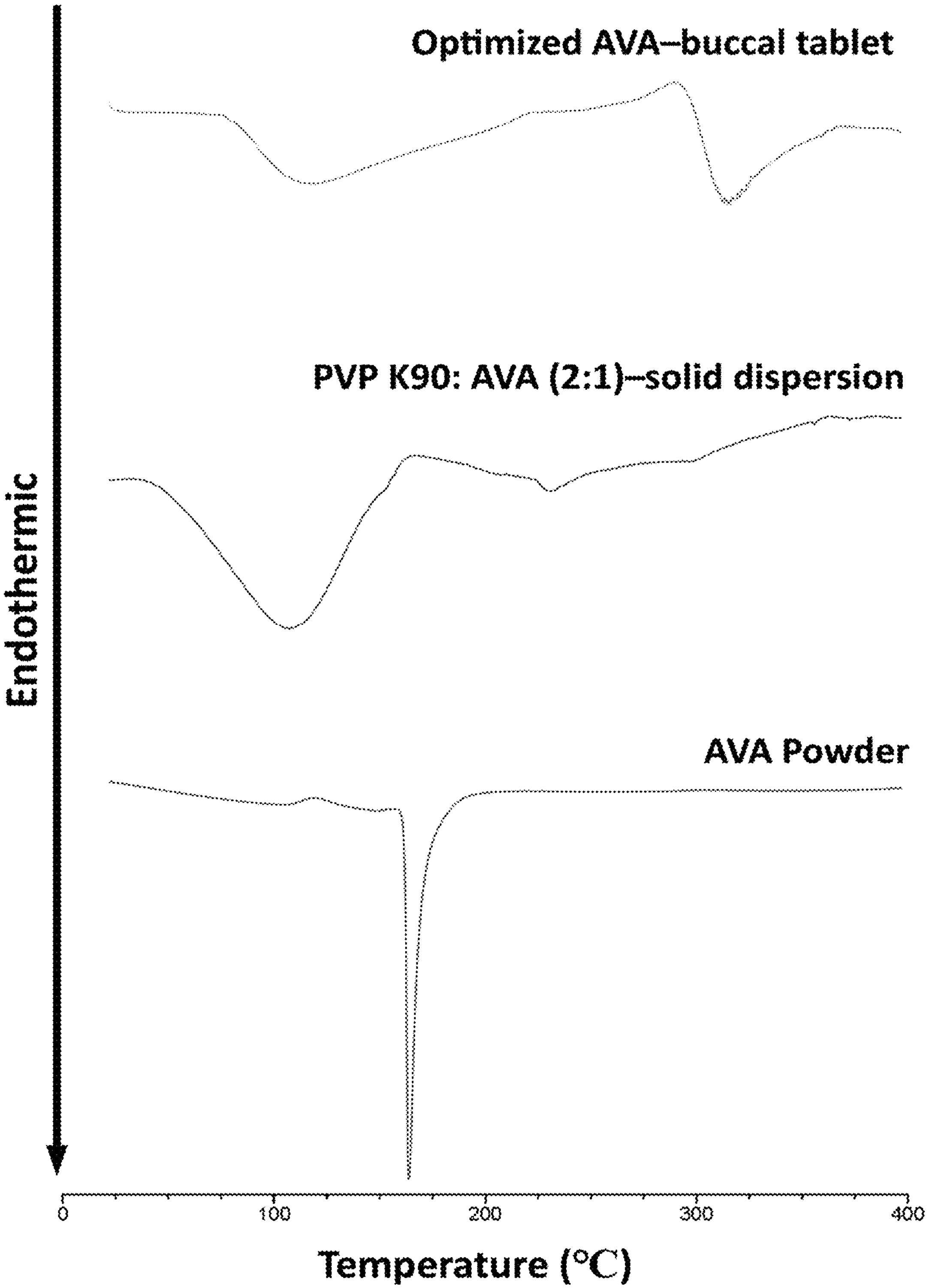
FIG. 7. DSC Thermograms of pure avanafil, avanafil solid dispersion with PVP K-90 (2:1 ratio), and the optimized buccal tablet.

FIG. 7 shows the DSC thermograms of raw AVA powder, PVP K90: AVA (2:1)—solid dispersion, and the optimized AVA—buccal tablet—formulation. The thermogram of AVA showed a sharp endothermic peak at 162° C. corresponding to the melting point of AVA. This peak indicates the crystalline nature of AVA. However, the characteristic peak of AVA disappeared in the DSC thermograms of the PVP K90: AVA (2:1)—solid dispersion and the optimized AVA—buccal tablet—formulation (FIG. 7), which is an indication of the possible drug physical change upon mixing with the solid dispersion ingredient (PVP K90) (64) and the buccal tablet excipients (48,65-68). This behavior may be attributed to the complete solubilization of the drug in the form of an amorphous state in the solid dispersion and buccal tablet mixture, as previously mentioned (69). The absence of the endothermic peak can also be attributed to the suppression of the thermal feature of the drug because of the formation of an amorphous solid solution (35).

In-vivo Pharmacokinetic Evaluation on Healthy Human Volunteers

All volunteers who participated in the study have fully completed the clinical research. The pharmacokinetic parameters of the clinical study are depicted in Table 5.

TABLE 5

In-vivo pharmacokinetic parameters of the optimized AVA buccal tablet and commercial AVA oral tablet.

| Parameters (unit) | Optimized AVA buccal tablet (± SD) | | Commercial AVA oral tablet (±SD) | |
|---|---|---|---|---|
| $K_{el}$ ($h^1$) | 0.035 | (±0.009) | 0.174 | (±0.112) |
| $t_{1/2}$ (h) | 20.528 | (±5.514) | 7.049 | (±7.181) |
| $T_{max}$ (h) | 8.667 ** | (±2.309) | 0.667 | (±0.289) |
| $C_{max}$ (ng/mL) | 314.137 | (±19.03) | 295 | (±65.383) |
| $AUC_{0-t}$ (ng/mL × h) | 11044.778 **** | (±892) | 1026.213 | (±41.155) |
| $AUC_{0-\infty}$ (ng/mL × h) | 12475.987 *** | (±1362.53) | 1138.002 | (±143.119) |
| $AUMC_{0-\infty}$ (ng/mL × $h^2$) | 437840.2 ** | (±117249.207) | 8485.468 | (±7528.117) |
| $MRT_{0-\infty}$ (h) | 34.77 ** | (±6.401) | 7.012 | (±5.388) |
| $V_d$ [(mg/kg)/(ng/mL)] | 0.118 | (±0.023) | 0.416 | (±0.378) |
| Cl ([(mg/kg)/(ng/mL)]/h) | 0.004 *** | (±4.705 × $10^{-4}$) | 0.044 | (±0.005) |

Note:
*, , *, and **** denote Significant different of values of the optimized AVA buccal tablet versus values of the oral commercial AVA tablet at $P < 0.05$, $P < 0.01$, $P < 0.001$, and $P < 0.0001$, respectively.

Figure 8:
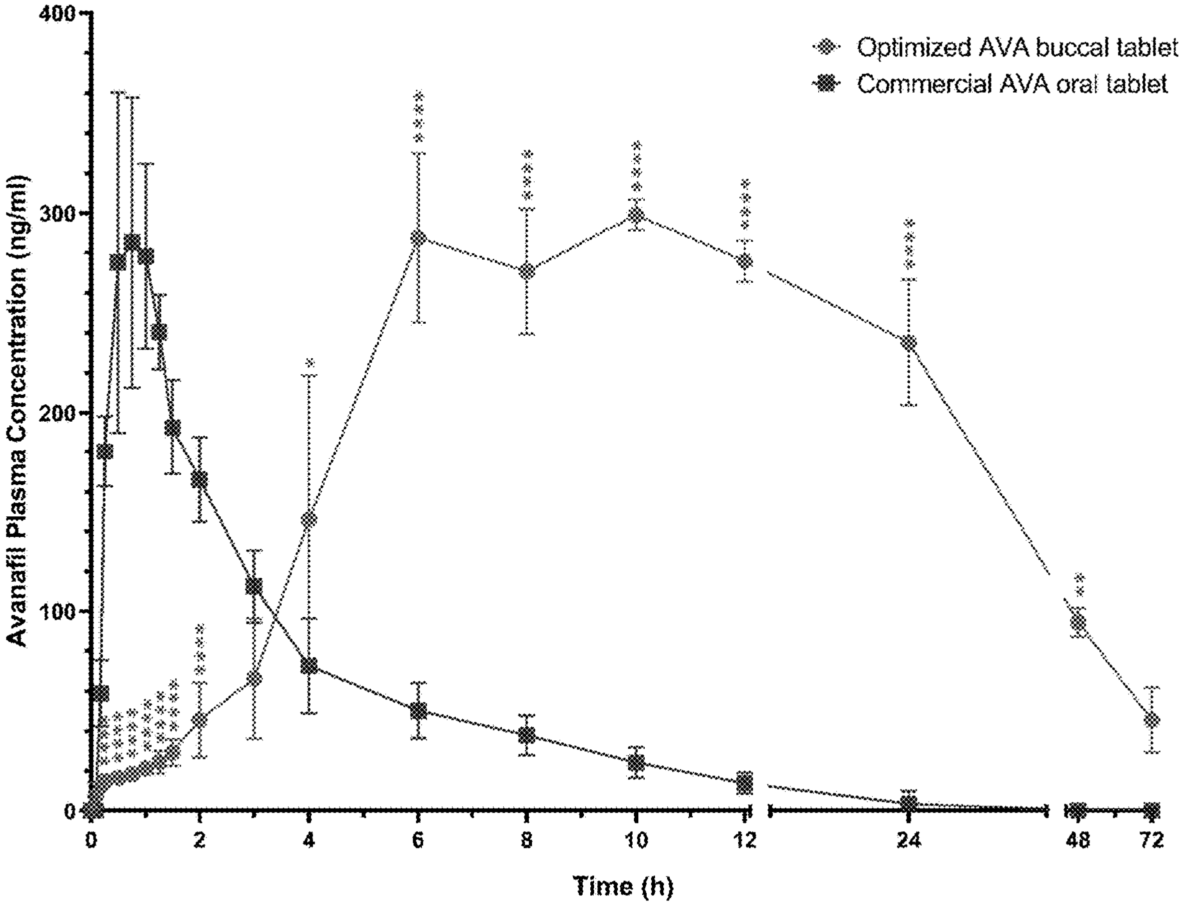
FIG. 8. The mean plasma concentration-time profiles of AVA after oral administration of a single dose (50 mg) of the marketed tablet and optimized buccal tablet.

FIG. 8 displayed the plasma concentration-time curve profiles after oral administration of the optimized AVA—buccal tablet compared to the marketed oral tablets. The results indicated that AVA's maximum plasma concentration ($C_{max}$) in the optimized AVA-buccal tablet was 314.137 ng/mL. This $C_{max}$ was obtained within 8.67 h ($T_{max}$).

On the other hand, the commercial oral tablets demonstrated a $C_{max}$ of 295 ng/mL after 0.67 h. Although the $C_{max}$ of AVA in the optimized AVA—buccal tablet was not significantly different from that of the commercial oral tablet, the optimized AVA—buccal tablet reached the maximum plasma concentration 8 h after the commercial oral tablet. In addition, the optimized AVA—buccal tablet produced significantly higher AVA plasma concentrations than the commercial oral tablet 4 h after administration to 48 h, confirming the prolonged therapeutic action duration. Amazingly, the optimized AVA—buccal tablet showed higher AUC compared to the commercial oral tablets, which indicates the improvement of the relative bioavailability of AVA in the optimized buccal tablet by 1076.27% over the commercial oral tablet. Furthermore, the two-tailed unpaired t-test revealed that $MRT_{0-\infty}$ of the optimized AVA—buccal tablet was found to be 4.96 folds higher than that of the commercial oral tablet ($P<0.01$), while the clearance (Cl) of the optimized AVA—buccal tablet was found to be 11 times lower than the Cl of the commercial oral tablet ($P<0.001$).

The improved absorption, bioavailability, and prolonged extent of the optimized AVA—buccal tablet can be understood through two correlated approaches. The first approach is the enhanced solubilization of the drug via utilization of PVP K90 solid dispersion, as well as the use of sodium deoxycholate as mucopenetration enhancer (70), and thus more availability of AVA to be absorbed, which is considered the first rate-limiting step for drug absorption in the BCS Class II compounds (71). The second approach is using the buccal route for delivery, depending on the limited surface area of the buccal cavity for absorption in comparison to the oral route (15). This feature is intentionally utilized to control the absorption and decrease the incidence of prompt high AVA plasma concentrations. In addition to utilizing this feature, using modified/optimized release mucoadhesive buccal tablets can be considered the second rate-limiting step for drug absorption (72). Therefore, changing the drug release from the optimized mucoadhesive AVA—buccal tablet to release the drug load over 8 h succeeded in achieving the revealed extended absorption of AVA over 72 h. This finding is expected to maximize the benefits, especially after circumventing the hepatic metabolism via the buccal route of administration.

Despite the fast onset achieved by the commercial oral tablet, it cannot be considered a superior effect over the 8 h delay in $T_{max}$ for the optimized AVA—buccal tablet. The latter behavior can potentially confirm much better control for AVA's therapeutic/pharmacological activity over a longer period. According to the chronic nature of any erectile dysfunction disorder (which requires treatment for 3 months up to 1-year duration (73,74)), the enhanced bioavailability via this novel approach, along with the prolonged duration of efficacy, will improve the convenience, adherence, and compliance for patients with erectile dysfunction.

REFERENCES

1. Selvin E, Burnett AL, Platz EA. Prevalence and Risk Factors for Erectile Dysfunction in the US. Am J Med. 2007 February; 120 (2):151-7.

2. Mulhall JP, Luo X, Zou KH, Stecher V, Galaznik A. Relationship between age and erectile dysfunction diagnosis or treatment using real-world observational data in the USA. Int J Clin Pract. 2016 December; 70 (12):1012-8.

3. Fahmy U. Nanoethosomal transdermal delivery of vardenafil for treatment of erectile dysfunction: optimization, characterization, and in vivo evaluation. Drug Des Devel Ther. 2015 November; 9:6129-37.

4. El-Sakka AI. Erectile dysfunction in Arab countries. Part I: Prevalence and correlates. Arab J Urol. 2012 Jun. 5; 10 (2):97-103.

5. Alamoudi AA, Ahmed OAA, El-Say KM. Investigating the potential of transdermal delivery of avanafil using vitamin e-tpgs based mixed micelles loaded films. Pharmaceutics. 2021 May 17; 13 (5):739.

6. Hackett G, Kirby M, Wylie K, Heald A, Ossei-Gerning N, Edwards D, et al. British Society for Sexual Medicine Guidelines on the Management of Erectile Dysfunction in Men-2017. J Sex Med. 2018 Apr. 15 (4):430-57.

7. Al-hejaili OD, Alamoudi AA, Ahmed OAA, El-Say KM. Transdermal Film Loaded with Avanafil Ultra-deformable Nanovesicles to Enhance its Percutaneous Absorption and Bioavailability. AAPS PharmSciTech. 2022 Jan. 4; 23:46.

8. Evans J, Burke R. Avanafil for treatment of erectile dysfunction: review of its potential. Vasc Health Risk Manag. 2012 August; 8:517-23.

9. Hosny KM, Ahmed OAA, Fahmy UA, Alkhalidi HM. Nanovesicular systems loaded with a recently approved second generation type-5 phospodiesterase inhibitor (avanafil): I. Plackett-Burman screening and characterization. J Drug Deliv Sci Technol. 2018 February; 43:154-9.

10. Patel VF, Liu F, Brown MB. Advances in oral transmucosal drug delivery. J Control Release. 2011 July; 153 (2):106-16.

11. Pather SI, Rathbone MJ, Şenel S. Current status and the future of buccal drug delivery systems. Expert Opin Drug Deliv. 2008 May 20; 5 (5):531-42.

12. Lesch CA, Squier CA, Cruchley A, Williams DM, Speight P. The Permeability of Human Oral Mucosa and Skin to Water. J Dent Res. 1989 Sep. 9; 68 (9):1345-9.

13. Owens TS, Dansereau RJ, Sakr A. Development and evaluation of extended release bioadhesive sodium fluoride tablets. Int J Pharm. 2005 January; 288 (1):109-22.

14. Takahashi Y, Takeda C, Seto I, Kawano G, Machida Y. Formulation and evaluation of lactoferrin bioadhesive tablets. Int J Pharm. 2007 October; 343 (1-2):220-7.

15. El-Say KM, Ahmed TA. Buccal Route of Drug Delivery. In: Talevi A, editor. The ADME Encyclopedia. Cham: Springer International Publishing; 2022. p. 222-31.

16. Zaki NM, Awad GAS, Mortada ND, Abd ElHady SS. Rapid-onset intranasal delivery of metoclopramide hydrochloride. Part I. Influence of formulation variables on drug absorption in anesthetized rats. Int J Pharm. 2006;327(1-2): 89-96.

17. LUDWIG A. The use of mucoadhesive polymers in ocular drug delivery. Adv Drug Deliv Rev. 2005 Nov. 3; 57 (11):1595-639.

18. Megahed MA, El-Sawy HS, Reda AM, Abd-Allah FI, Abu Elyazid SK, Lila AE, et al. Effect of nanovesicular surface-functionalization via chitosan and/or PEGylation on cytotoxicity of tamoxifen in induced-breast cancer model. Life Sci. 2022;307(May):120908.

19. El-Say KM, El-Sawy HS. Polymeric nanoparticles: Promising platform for drug delivery. Int J Pharm. 2017 August; 528 (1-2):675-91.

20. El-Say KM, Al-hejaili OD, Alamoudi AA, Ahmed OAA. Transfersome-containing transdermal film formulations and methods of use. United States Patent and Trademark Office. KSA; U.S. Pat. No. 11,185,513 B1, 2021.

21. Mosli HAM, Atteiah SAG, Omar KMH, El-Bassossy HMAE-M, Helal MHAM. In situ gel loaded with phosphodiesterase type V inhibitors nanoemulsion. United States Patent Application Publication. KSA; US 2015/0099751 A1, 2015.

22. Broman CT, Sheu E. Orally disintegrating dosage form for administration of avanafil, and associated methods of manufacture and use. United States; U.S. Pat. No. 10,028, 916 B2, 2018.

23. Fossel ET, Gutman L. Transdermal delivery of sildenafil and other phosphodiesterase type 5 inhibitors. United States Patent Application Publication. USA; US 2016/0067252 A1, 2016.

24. Ahmed OAA, Badr-Eldin SM. Development of an optimized avanafil-loaded invasomal transdermal film. United States Patent and Trademark Office. U.S. Pat. No. 10,751,294 B1, 2020.

25. Al-hejaili OD, Alamoudi AA, Ahmed OAA, El-Say KM. Transdermal Film Loaded with Avanafil Ultra-deformable Nanovesicles to Enhance its Percutaneous Absorption and Bioavailability. AAPS PharmSciTech. 2022 Jan. 4; 23 (1):46.

26. Ahmed OAA, Badr-Eldin SM. Development of an optimized avanafil-loaded invasomal transdermal film: Ex vivo skin permeation and in vivo evaluation. Int J Pharm. 2019;570:118657.

27. Kurakula M, Naveen N. R, Patel B, Manne R, Patel DB. Preparation, optimization and evaluation of chitosan-based avanafil nanocomplex utilizing antioxidants for enhanced neuroprotective effect on PC12 cells. Gels. 2021; 7 (3).

28. Fahmy UA, Ahmed OAA, Hosny KM. Development and evaluation of avanafil self-nanoemulsifying drug delivery system with rapid onset of action and enhanced bioavailability. AAPS PharmSciTech. 2015 February; 16 (1): 53-8.

29. Aldawsari HM, Fahmy UA, Abd-Allah F, Ahmed OAA. Formulation and optimization of avanafil biodegradable polymeric nanoparticles: A single-dose clinical pharmacokinetic evaluation. Pharmaceutics. 2020 Jun. 26; 12 (6):596.

30. Soliman KAB, Ibrahim HK, Ghorab MM. Formulation of avanafil in a solid self-nanoemulsifying drug delivery system for enhanced oral delivery. Eur J Pharm Sci. 2016; 93:447-55.

31. Gardouh AR, Elhusseiny S, Gad S. Mixed Avanafil and Dapoxetin Hydrochloride cyclodextrin nano-sponges: Preparation, in-vitro characterization, and bioavailability determination. J Drug Deliv Sci Technol. 2022; 68 (December 2021):103100.

32. Kurakula M, Ahmed OAA, Fahmy UA, Ahmed TA. Solid lipid nanoparticles for transdermal delivery of avanafil: optimization, formulation, in-vitro and ex-vivo studies. J Liposome Res. 2016; 26 (4):288-96.

33. Sinha S, Ali M, Baboota S, Ahuja A, Kumar A, Ali J. Solid Dispersion as an Approach for Bioavailability Enhancement of Poorly Water-Soluble Drug Ritonavir. AAPS PharmSciTech. 2010 Jun 18; 11 (2):518-27.

34. El-Say K, Al-Subaie M, Hosny K, Ahmed T, Aljaeid B. Utilization of nanotechnology to enhance percutaneous absorption of acyclovir in the treatment of herpes simplex viral infections. Int J Nanomedicine. 2015 June; 10:3973.

35. Alotaibi FO, Alhakamy NA, Omar AM, El-Say KM. Clinical Pharmacokinetic Evaluation of Optimized Liquisolid Tablets as a Potential Therapy for Male Sexual Dysfunction. Pharmaceutics. 2020 Dec. 7; 12 (12):1187.

36. Desoqi MH, El-sawy HS, Kafagy E, Ghorab M, Gad S. Fluticasone propionate-loaded solid lipid nanoparticles with augmented anti-inflammatory activity : optimisation , characterisation and pharmacodynamic evaluation on rats. J Microencapsul. 2021; 38 (3):177-91.

37. Kassem MA, El-Sawy HS, Abd-Allah FI, Abdelghany TM, El-Say KM. Maximizing the Therapeutic Efficacy of Imatinib Mesylate-Loaded Niosomes on Human Colon Adenocarcinoma Using Box-Behnken Design. J Pharm Sci. 2017; 106:111-22.

38. Soliman MS, Abd-Allah FI, Hussain T, Saeed NM, El-Sawy HS. Date seed oil loaded niosomes: development, optimization and anti-inflammatory effect evaluation on rats. Drug Dev Ind Pharm. 2018 Jul. 3; 44 (7):1185-97.

39. El-Say KM, Ahmed TA, El-Sawy HS. Transdermal film formulations and methods of use. KSA: United States Patent; U.S. Pat. No. 11,096,902 B1, 2021.

40. Gardouh AR, Ewedah TM, Abd-allah FI, Ghorab MM, Omran MM, El-sawy HS. Enhanced efficacy , cellular uptake , and antiangiogenic activity of the optimized imatinib mesylate-loaded proniosomal-derived nanovesicles. J Drug Deliv Sci Technol. 2021; 61:102267.

41. Yan X, Gurtler J, Fratamico P, Hu J, Gunther NW, Juneja V, et al. Comprehensive Approaches to Molecular Biomarker Discovery for Detection and Identification of Cronobacter spp. (Enterobacter sakazakii) and Salmonella spp. Appl Environ Microbiol. 2011 March; 77 (5):1833-43.

42. Nair AB, Kumria R, Harsha S, Attimarad M, Al-Dhubiab BE, Alhaider IA. In vitro techniques to evaluate buccal films. J Control Release. 2013 February; 166 (1):10-21.

43. Ahmed TA, Alotaibi HA, Alharbi WS, Safo MK, El-Say KM. Development of 3D-Printed, Liquisolid and Directly Compressed Glimepiride Tablets, Loaded with Black Seed Oil Self-Nanoemulsifying Drug Delivery System: In Vitro and In Vivo Characterization. Pharmaceuticals. 2022 Jan. 5; 15 (1):68.

44. Silva CO, Rijo P, Molpeceres J, Figueiredo IV, Ascensão L, Fernandes AS, et al. Polymeric nanoparticles modified with fatty acids encapsulating betamethasone for anti-inflammatory treatment. Int J Pharm. 2015 September; 493 (1-2):271-84.

45. Mulik RS, Mönkkönen J, Juvonen RO, Mahadik KR, Paradkar AR. ApoE3 mediated polymeric nanoparticles containing curcumin: Apoptosis induced in vitro anticancer activity against neuroblastoma cells. Int J Pharm. 2012 November; 437 (1-2):29-41.

46. Abo-EL-Sooud K. Absolute and Relative Bioavailability. In: Hock FJ, Gralinski MR, editors. Drug Discovery and Evaluation: Methods in Clinical Pharmacology. Cham: Springer International Publishing; 2018. p. 1-7.

47. Asbahr ACC, Franco L, Barison A, Silva CWP, Ferraz HG, Rodrigues LNC. Binary and ternary inclusion complexes of finasteride in HPβCD and polymers: Preparation and characterization. Bioorg Med Chem. 2009 April; 17 (7):2718-23.

48. Soliman KA, Ibrahim HK, Ghorab MM. Effect of different polymers on avanafil-β-cyclodextrin inclusion complex: in vitro and in vivo evaluation. Int J Pharm. 2016 October; 512 (1):168-77.

49. El-Say KM, Ahmed TA, Aljefri AH, El-Sawy HS, Fassihi R, Abou-Gharbia M. Oleic acid-reinforced PEGylated polymethacrylate transdermal film with enhanced antidyslipidemic activity and bioavailability of atorvastatin: A mechanistic ex-vivo/in-vivo analysis. Int J Pharm. 2021; 608:121057.

50. Harbi I, Aljaeid B, El-Say KM, Zidan AS. Glycosylated sertraline-loaded liposomes for brain targeting: QbD study of formulation variabilities and brain transport. AAPS PharmSciTech. 2016; 17 (6):1404-20.

51. Liu J, Wang J, Leung C, Gao F. A multi-parameter optimization model for the evaluation of shale gas recovery enhancement. Energies. 2018; 11 (3):654.

52. Basahih TS, Alamoudi AA, El-Say KM, Alhakamy NA, Ahmed OAA. Improved Transmucosal Delivery of Glimepiride via Unidirectional Release Buccal Film Loaded With Vitamin E TPGS-Based Nanocarrier. Dose-Response. 2020 Jul. 1; 18 (3):155932582094516.

53. Hoffmann A, Daniels R. A novel test system for the evaluation of oral mucoadhesion of fast disintegrating tablets. Int J Pharm. 2018 November; 551 (1-2):141-7.

54. Ahmed TA, Bawazir AO, Alharbi WS, Safo MK. Enhancement of simvastatin ex vivo permeation from mucoadhesive buccal films loaded with dual drug release carriers. Int J Nanomedicine. 2020; 15:4001-20.

55. Avranas A, Tasopoulos V. Aqueous Solutions of Sodium Deoxycholate and Hydroxypropylmethylcellulose: Dynamic Surface Tension Measurements. J Colloid Interface Sci. 2000 January; 221 (2):223-9.

56. Guo Y, Wang R, Shang Y, Liu H. Effects of polymers on the properties of hydrogels constructed using sodium deoxycholate and amino acid. RSC Adv. 2018; 8 (16):8699-708.

57. Tank D, Karan K, Gajera BY, Dave RH. Investigate the effect of solvents on wet granulation of microcrystalline cellulose using hydroxypropyl methylcellulose as a binder and evaluation of rheological and thermal characteristics of granules. Saudi Pharm J. 2018 May; 26 (4):593-602.

58. Vila-Jato J, Concheiro A, Seijo B, Viana B. Aging of nitrofurantoin tablets containing Carbopol 934 as a binder. Int J Pharm. 1986 June; 30 (2-3):229-36.

59. De Simone V, Dalmoro A, Lamberti G, Caccavo D, D'Amore M, Barba AA. Effect of binder and load solubility properties on HPMC granules produced by wet granulation process. J Drug Deliv Sci Technol. 2019 February; 49 (September 2018):513-20.

60. Chen C, Lee SH, Cho M, Kim J, Lee Y. Cross-Linked Chitosan as an Efficient Binder for Si Anode of Li-ion Batteries. ACS Appl Mater Interfaces. 2016 Feb. 3; 8 (4):2658-65.

61. Kurakula M, Rao GSNK. Pharmaceutical assessment of polyvinylpyrrolidone (PVP): As excipient from conventional to controlled delivery systems with a spotlight on COVID-19 inhibition. J Drug Deliv Sci Technol. 2020 December; 60 (June):102046.

62. Kapoor B, Gupta R, Gulati M, Singh SK, Khursheed R, Gupta M. The Why, Where, Who, How, and What of the vesicular delivery systems. Adv Colloid Interface Sci. 2019; 271:101985.

63. Attia KAM, Mohamad AA, Emara MS, Abdel-Raoof AM, Hasan MA, Madkour AW, et al. Second derivative synchronous fluorescence determination of avanafil in the presence of its acid-induced degradation product aided by powerful Lean Six Sigma tools augmented with D-optimal design. RSC Adv. 2021; 11 (7):3834-42.

64. Teoh X, Yeoh Y, Yoong L, Chan S. Sustainable Dissolution Performance of a Carrier Tailored Electrospun. Pharm Res. 2020 Feb. 7; 37 (2):28.

65. Rani NS, Sannappa J, Demappa T, Mahadevaiah. Effects of CdCl2 concentration on the structural, thermal and ionic conductivity properties of HPMC polymer electrolyte films. Ionics (Kiel). 2015 Jan. 27; 21 (1):133-40.

66. Ahmed S, Kassem MA, Sayed S. Bilosomes as Promising Nanovesicular Carriers for Improved Transdermal Delivery: Construction, in vitro Optimization, ex vivo Permeation and in vivo Evaluation. Int J Nanomedicine. 2020 December; Volume 15:9783-98.

67. Bayón R, Rojas E. Feasibility study of D-mannitol as phase change material for thermal storage. AIMS Energy. 2017; 5 (3):404-24.

68. Zolotov SA, Demina NB, Zolotova AS, Shevlyagina N V., Buzanov GA, Retivov VM, et al. Development of novel darunavir amorphous solid dispersions with mesoporous carriers. Eur J Pharm Sci. 2021 April; 159 (October 2020):105700.

69. Ahmed TA. Formulation and clinical investigation of optimized vinpocetine lyoplant-tabs: new strategy in development of buccal solid dosage form. Drug Des Devel Ther. 2018 December; Volume 13:205-20.

70. Dadashzadeh S, Haeri A, Daeihamed M, Arzani G, Bakhtiari Kaboutaraki H.

Niosomal carriers enhance oral bioavailability of carvedilol: effects of bile salt-enriched vesicles and carrier surface charge  Int J Nanomedicine. 2015 July; 10:4797.

71. Davanço MG, Campos DR, Carvalho P de O. In vitro—In vivo correlation in the development of oral drug formulation: A screenshot of the last two decades. Int J Pharm. 2020 April; 580:119210.

72. Cardot JM, Garrait G, Beyssac E. Use of IVIVC to Optimize Generic Development. Dissolution Technol. 2015; 22 (2):44-8.

73. Kedia GT, Ückert S, Assadi-Pour F, Kuczyk MA, Albrecht K. Avanafil for the treatment of erectile dysfunction: initial data and clinical key properties. Ther Adv Urol. 2013 Feb. 21; 5 (1):35-41.

74. Hellstrom W, Katz E, Tan R, Rittenberg D. Avanafil for erectile dysfunction in elderly and younger adults: differential pharmacology and clinical utility. Ther Clin Risk Manag. 2014 August; 10 (1):701-11.

Acknowledgment of Sponsored Research

This invention was funded by the Deanship of Scientific Research (DSR) at King Abdulaziz University, Jeddah, under grant no. (RG-39-166-43). Therefore, inventors acknowledge with thanks the DSR for technical and financial support.

The invention claimed is:

1. A method of preparing a buccal tablet formulation, comprising
    mixing a specified amount of solid dispersion of avanafil and PVP K-90, a specified amount of hydroxypropyl methylcellulose, a predetermined amount of sodium deoxycholate, porous silicon dioxide, and mannitol and then passing through mesh sieves to form a powder blend;
    de-lumping a talc powder and magnesium stearate through a sieve and adding retrieved talc powder to the powder blend;
    mixing the talc powder mixture and the powder blend to form a dry mixture; and
    compressing the dry mixture to form a buccal tablet,
    wherein the buccal tablet formulation comprises
    100 mg of polyvinylpyrrolidone K-90 (PVP K-90);
    36 mg of hydroxypropyl methylcellulose functioning in the buccal tablet formulation as a mucoadhesive polymer;
    a sodium deoxycholate functioning in the buccal tablet formulation as a mucopenetration enhancer;
    10 mg of porous silicon dioxide;
    4 mg of mannitol; and
    50 mg of avanafil,
    wherein the PVP K-90 to avanafil ratio ranges from 2.3:1 to 1.7:1.

2. The method of claim 1, wherein the PVP K-90 to avanafil ratio is 2:1.

* * * * *